(12) United States Patent
Alberati et al.

(10) Patent No.: US 9,187,455 B2
(45) Date of Patent: Nov. 17, 2015

(54) SUBSTITUTED PYRIDAZINES AS PDE10A INHIBITORS

(75) Inventors: Daniela Alberati, Zofingen (CH); Matthias Koerner, Grenzach-Wyhlen (DE); Bernd Kuhn, Reinach BL (CH); Jens-Uwe Peters, Grenzach-Wyhlen (DE); Rosa Maria Rodriguez Sarmiento, Basel (CH); Mark Rogers-Evans, Bottmingen (CH); Markus Rudolph, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 531 days.

(21) Appl. No.: 12/705,988

(22) Filed: Feb. 16, 2010

(65) Prior Publication Data

US 2010/0216793 A1 Aug. 26, 2010

(30) Foreign Application Priority Data

Feb. 23, 2009 (EP) ..................................... 09153391

(51) Int. Cl.
*A61K 31/501* (2006.01)
*C07D 237/04* (2006.01)
*C07D 403/14* (2006.01)

(52) U.S. Cl.
CPC ..................................... *C07D 403/14* (2013.01)

(58) Field of Classification Search
CPC ............................. A61K 31/501; C07D 237/04
USPC ..................... 544/238, 114, 359; 514/252.05; 548/373.1; 549/362, 434; 546/148, 546/152, 268.1
See application file for complete search history.

(56) References Cited

U.S. PATENT DOCUMENTS

2004/0058918 A1* 3/2004 Dominguez et al. ........ 514/227.8
2010/0331339 A9* 12/2010 Guzzo et al. ............. 514/252.04

FOREIGN PATENT DOCUMENTS

| EP | 1553096 | 7/2005 |
|---|---|---|
| WO | 2005012485 | 2/2005 |
| WO | 2007/129183 | 11/2007 |
| WO | 2010063610 | 6/2010 |

OTHER PUBLICATIONS

The Japanese Office Action, issued on May 14, 2013, in the corresponding Japanese application No. 2011-550576., pp. 5.
Lewis et al., Neuron. vol. 28 pp. 325-333 (2000).
Vandenberg et al., Exp. Opin. Ther. Targets vol. 5(4) pp. 597-518 (2001).
Nakazato et al., Exp. Opin Ther Patents vol. 10(1) pp. 75-98 (2000).
Sharma T., Br. J. Psychiatry, vol. 174 (Suppl. 28) pp. 44-51 (1999).
Javitt et al., Biol. Psychiatry vol. 45, pp. 668-679 (1999).
Beavo J., Physiol. Rev. vol. 75, pp. 725-748 (1995).
Conti et al., Prog. Nucleic Acid Res. Mol, Biol. vol. 63, pp. 1-38 (1999).
Soderling et al., Curr. Opin. Cell. Biol. vol. 12, pp. 174-179 (2000).
Manallack et al, J. Med Chem. vol. 48(10) pp. 3449-3462 (2005).
Fujishige et al., Eur. J. Biochem. vol. 266(3) pp. 1118-1127 (1999).
Soderling et al., Proc. Natl. Acad. Sci. USA, vol. 96/12 pp. 7071-7076 (1999).
Loughney et al., Gene vol. 234(1) pp. 109-117 (1999).
Fujishige et al,, J. Biol. Chem. vol. 274 pp. 18438-18445 (1999).
Coskran et al., J. Histochem Cytochem vol. 54(11) pp. 1205-1213 (2006).
Seeger et al., Brain Res vol. 985 pp. 113-126 (2003).
Graybiel A. M., Curr. Biol. vol. 10, pp. R509-R511 (2000).
Siuciak et al., Neuropharmacology vol. 51(2) pp. 386-396 (2006).
Siuciak et al., Neuropharmacology vol. 51(2) pp. 374-385 (2006).
Rodefer et al., Eur. J. Neuroscience vol. 2, pp. 1070-1076 (2005).
Sano, H. J., Neurochem, vol. 105 pp. 546-556 (2008).

* cited by examiner

*Primary Examiner* — Douglas M Willis

(57) ABSTRACT

The present invention is concerned with novel pyridazinone derivatives of formula (I)

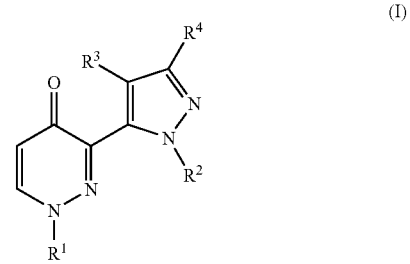

wherein $R^1$, $R^2$, $R^3$ and $R^4$ are as defined in the description and in the claims, as well as physiologically acceptable salts and esters thereof. These compounds inhibit PDE10A and can be used as pharmaceuticals.

24 Claims, No Drawings

SUBSTITUTED PYRIDAZINES AS PDE10A INHIBITORS

PRIORITY TO RELATED APPLICATION(S)

This application claims the benefit of European Patent Application No. 09153391.9, filed Feb. 23, 2009, which is hereby incorporated by reference in its entirety.

SEQUENCE LISTING

The instant application contains a Sequence Listing which has been submitted via EFS-Web and is hereby incorporated by reference in its entirety. Said ASCII copy, created on Mar. 31, 2010, is named 25929.txt, and is 977 bytes in size.

The catalytic domain of human PDE10A2, residues serine 449 to aspartate 789, was amplified by PCR using cDNA (Origene) and the oligonucleotides 5'-GGGGA-CAAGTTTGT ACAAAAAAGCAGGCTTAGTACCTA-GAGGATCAAGCA TTTGTACTTCAGAAG-3' (SEQ ID NO: 1) (with AttB1 recombination site in bold and thrombin protease cleavage site in italics) and 5'GGGGACCACTTTG-TACAAGAA AGCTGGGTCAATCTTCAGATGCAGCTG-3' (SEQ ID NO: 2) (with AttB2 recombination site in bold) which conferred Gateway recombination sites. The PCR product was used in a BP recombination reaction with pDONR221 to generate pENTR Thm-PDE10A2(S449-D789) which was DNA sequence verified and then used in an LR recombination reaction with a Gateway modified version of pET11a. The resulting expression vector, placT7.2 H6-(gwl)-Thm-PDE10A2(S449-D789) was DNA sequence confirmed and transformed into *E. coli* strain BL21(DE3) pLysS and recombinant protein was produced in TB medium at 20° C. by induction to a final IPTG concentration of 0.5 mM at an optical density of 1.0 at 600 nm for 20 hours. About 30% of the protein was in the soluble fraction of the cell homogenate. The protein was purified using sequential chromatography on Ni-NTA and HiTrapQ/HiTrapS. After thrombin digest at room temperature a HiTrapChelating/HiTrap Benzamindin chromatography removed impurities, uncleaved protein and thrombin. Final purification of PDE10A2(S449-D789) was performed on a Superdex 75 size exclusion chromatography equilibrated with 25 mM HEPES pH 8.4, 0.15 M NaCl. The yield of pure protein was 2 mg/liter of culture volume is relatively low. The purity of the protein was >95%, monomeric and monodisperse as shown by SDS-PAGE, HPLC and analytical ultracentrifugation.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach, besides ameliorating positive symptoms in schizophrenic patients, poorly addresses negative and cognitive symptoms which are the best predictors of functional outcome (Sharma T., *Br. J. Psychiatry*, 174(suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., *Biol. Psychiatry*, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAPM and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., *Physiol. Rev.* 1995, 75, 725-748; Conti, M., Jin, S. L., *Prog. Nucleic Acid Res. Mol. Biol.* 1999, 63, 1-38; Soderling, S. H., Beavo, J. A., *Curr. Opin. Cell Biol.* 2000, 12, 174-179, Manallack, D. T. et al. *J. Med. Chem.* 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., *Eur J Biochem* (1999) 266(3):1118-1127, Soderling S. H., et al., *Proc Natl Acad Sci USA* (1999) 96(12):7071-7076, Loughney K., et al., *Gene* (1999) 234(1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., *J. Biol. Chem.* 1999, 274, 18438-18445, Sweet, L. (2005) WO 2005/012485). On the other hand expression of PDE10A protein has been observed only in enteric ganglia, in testis and epididdimal sperm (Coskran T. M, et al., *J. Histochem. Cytochem.* 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., *Eur. J. Biochem.* 1999, 266, 1118-1127; Seeger, T. F. et al., *Brain Res.* 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. *Curr. Biol.* 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition Inhibition of this enzyme pharmacologically or through gene disruption causes a reduction in activity and a reduced response to psychomotor stimulants. Inhibition also reduces the conditioned avoidance response, a behavioural response that is predictive of clinical antipsychotic activity (Siuciak, J. A.; et al., *Neuropharmacology* 2006, 51 (2), 386-396; Siuciak, J. A.; et al., *Neuropharmacology* 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., *Eur. J. Neuroscience* 2005, 2: 1070-1076). In addition increased social interaction in PDE10A2-deficient mice have been observed (Sano, H. *J. Neurochem.* 2008, 105, 546-556).

SUMMARY OF THE INVENTION

The invention provides novel pyridazinones of formula (I)

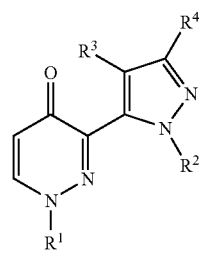

(I)

wherein
$R^1$ is heteroaryl which is optionally substituted with 1 to 4 substituents independently selected from the group consisting of lower-alkyl, lower-alkoxy, fluoro-lower-alkyl, fluoro-lower-alkoxy, lower-alkyl-$SO_2$, fluoro-lower-alkyl-$SO_2$, halogen, lower-alkoxy-lower-alkyl, cyano, $NO_2$, morpholinyl, $NH_2$—$SO_2$, N(H,lower-alkyl)-$SO_2$, N(lower-alkyl)$_2$-$SO_2$, pyrrolidinyl-$SO_2$, piperidinyl-$SO_2$, morpholinyl-$SO_2$, hydroxy, COOH, COO-lower-alkyl, lower-alkyl-C(O)O, CO-lower-alkyl, $CONH_2$, CON(H, lower-alkyl), CON(lower-alkyl)$_2$, lower-alkyl-CO—NH, lower-alkyl-CO—N(lower-alkyl), $NH_2$—CO-lower-alkyl, NH(lower-alkyl)-CO-lower-alkyl, N(lower-alkyl)$_2$-CO-lower-alkyl, $NH_2$, N(H,lower-alkyl), N(lower-alkyl)$_2$, $NH_2$-lower-alkyl, N(H,lower-alkyl)-lower-alkyl, N(lower-alkyl)$_2$-lower-alkyl, cycloalkyl, piperidinyl, piperazinyl and (N-lower-alkyl)-piperazinyl;

$R^2$ is aryl or heteroaryl, each of which is optionally substituted with 1 to 4 substituents independently selected from the group consisting of halogen, cyano, lower-alkyl, lower-alkoxy, fluoro-lower-alkyl, lower-alkinyl, lower-alkyl-$SO_2$, COOH, $CONH_2$, $NH_2$—$SO_2$, COO-lower-alkyl, lower-alkoxy-lower-alkyl, CON(H,lower-alkyl), CON (lower-alkyl)$_2$, N(H,lower-alkyl)-$SO_2$, N(lower-alkyl)$_2$-$SO_2$, lower-alkenyl, hydroxy, $NO_2$, morpholinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), $NH_2$—CO-lower-alkyl, NH(lower-alkyl)-CO-lower-alkyl, N(lower-alkyl)$_2$-CO-lower-alkyl, CO-lower-alkyl, $NH_2$, N(H,lower-alkyl), N(lower-alkyl)$_2$, $NH_2$-lower-alkyl, N(H,lower-alkyl)-lower-alkyl, N(lower-alkyl)$_2$-lower-alkyl, tri(lower-alkyl) silyl-lower-alkinyl and cycloalkyl, or wherein two substituents at adjacent positions on the aryl or heteroaryl are bound together to form a ring and said two bound substituents are lower-alkylene, dioxo-lower-alkylene, dioxofluoro-lower-alkylene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

$R^3$ is hydrogen, lower-alkyl, fluoro-lower-alkyl, lower-alkoxy, fluoro-lower-alkoxy, halogen, hydroxy or phenyl; and $R^4$ is hydrogen, lower-alkyl, fluoro-lower-alkyl, lower-alkoxy, fluoro-lower-alkoxy, halogen, hydroxy or phenyl; and pharmaceutically acceptable salts and esters thereof Further, the invention provides a process for the manufacture of the above compounds, pharmaceutical compositions which contain such compounds as well as methods for the manufacture these compounds and pharmaceutical compositions.

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The compounds of the present invention are also suitable for the treatment of diabetes and related disorders such as obesity by regulating the cAMP signaling system.

PDE10A inhibitors might also be useful in preventing neurons from undergoing apoptosis by raising cAMP and cGMP levels and, thus, might possess anti-inflammatory properties.

Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "alkenyl", alone or in combination with other groups, stands for a straight-chain or branched hydrocarbon residue comprising an olefinic bond and up to 20, preferably up to 16 carbon atoms. The term "lower-alkenyl" refers to a straight-chain or branched hydrocarbon residue comprising an olefinic bond and up to 7, preferably up to 4 carbon atoms, such as e.g. ethenyl or 2-propenyl.

The term "alkinyl" is the same as "alkynyl" and alone or in combination with other groups stands for a straight-chain or branched hydrocarbon residue comprising a triple bond and up to 20, preferably up to 16 carbon atoms. The term "lower-alkinyl" refers to a straight-chain or branched hydrocarbon residue comprising a triple bond and up to 7, preferably up to 4 carbon atoms, such as e.g. ethinyl or 2-propinyl.

The term "lower-alkylene", alone or in combination with other groups, refers to a branched or straight chain divalent lower-alkyl radical. This term is further exemplified by such radicals as methylene, ethylene, propylene and the like. The term "dioxo-lower-alkylene" refers to the group —O-lower-alkylene-O—.

The term "fluoro-lower-alkylene", alone or in combination with other groups, refers to a branched or straight chain divalent fluoro-lower-alkyl radical. This term is further exemplified by such radicals as —$CF_2$— and the like. The term "dioxo-fluoro-lower-alkylene" refers to the group —O-fluoro-lower-alkylene-O—.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "aryl", alone or in combination, refers to a phenyl or naphthyl group, preferably a phenyl group, which is optionally substituted, unless specifically stated otherwise, by 1 to 5, preferably 1 to 3, substituents, independently selected from the group consisting of halogen, hydroxy, amino, $NO_2$, lower-alkyl, hydroxy-lower-alkyl, lower-alkoxy, carboxy, carboxy-lower-alkyl, $H_2NC(O)$, (H,lower-alkyl)NC(O), (lower-alkyl)$_2$NC(O), fluoro-lower-alkyl, lower-alkyl-$SO_2$, lower-alkyl-$SO_2O$, lower-alkyl-$SO_2$—NH, lower-alkyl-$SO_2$—N(lower-alkyl), $H_2NSO_2$, (H,lower-alkyl)$NSO_2$, (lower-alkyl)$_2NSO_2$, cyano, heteroaryl, cycloalkyl, phenyl and phenyloxy. Preferred substituents can be halogen, lower-alkyl and lower-alkoxy. Furthermore, aryl groups can preferably be substituted as described in the description and claims below. Examples of aryl, wherein two substituents at adjacent positions on the aryl are bound together to form a ring and said two bound substituents are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene are e.g. tetrahydronaphthaline, indane, benzocycloheptene, benzo[1,3]dioxole, 2,3-dihydro-benzo[1,4]dioxine, 3,4-dihydro-2H-benzo[b][1,4]dioxepine, 2,2-difluoro-benzo[1,3]dioxole, 2,3-dihydro-1H-indole, 2,3-dihydro-1H-isoindole, 1,3-dihydro-indol-2-one, 1,3-dihydro-isoindol-2-one, 1,2,3,4-tetrahydroquinoline or 1,2,3,4-tetrahydroisoquinoline, preferably benzo[1,3]dioxole, 2,2-difluoro-benzo[1,3]dioxole or 2,3-dihydro-benzo[1,4]dioxine.

The term "heteroaryl" refers to an aromatic 5 to 6 membered monocyclic ring or 9 to 10 membered bicyclic ring which comprises 1, 2 or 3 atoms selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl and isoquinolinyl. Preferred heteroaryl groups are pyridinyl, quinolinyl and isoquinolinyl. Unless specifically stated otherwise, a heteroaryl group can optionally have a substitution pattern as described earlier in connection with the term "aryl". Furthermore, heteroaryl groups can preferably be substituted as described in the description and claims below. Preferred examples of heteroaryl, wherein two substituents at adjacent positions of the heteroaryl are bound together to form a ring are those wherein said two bound substituents are lower-alkylene, dioxo-lower-alkylene or dioxo-fluoro-lower-alyklene, e.g. 6,7-dihydro-5H-[2]pyridine, 5,6,7,8-tetrahydroisoquinoline, 5,6,7,8-tetrahydroquinoline, [1,3]dioxolo[4,5-c]pyridine, 2,2-difluoro-[1,3]dioxolo[4,5-c]pyridine, 2,3-dihydro-[1,4]dioxino[2,3-c]pyridine, preferably 5,6,7,8-tetrahydroisoquinoline.

Compounds of formula (I) can form pharmaceutically acceptable acid addition salts. Examples of such pharmaceutically acceptable salts are salts of compounds of formula (I)

with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts. Salts obtained by the addition of an acid are preferred.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

"Therapeutically effective amount" means an amount that is effective to prevent, alleviate or ameliorate symptoms of disease or prolong the survival of the subject being treated.

In detail, the present invention provides compounds of formula (I)

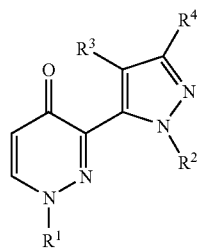

(I)

wherein
$R^1$ is heteroaryl which is optionally substituted with 1 to 4 substituents independently selected from the group consisting of lower-alkyl, lower-alkoxy, fluoro-lower-alkyl, fluoro-lower-alkoxy, lower-alkyl-$SO_2$, fluoro-lower-alkyl-$SO_2$, halogen, lower-alkoxy-lower-alkyl, cyano, $NO_2$, morpholinyl, $NH_2$—$SO_2$, N(H,lower-alkyl)-$SO_2$, N(lower-alkyl)$_2$-$SO_2$, pyrrolidinyl-$SO_2$, piperidinyl-$SO_2$, morpholinyl-$SO_2$, hydroxy, COOH, COO-lower-alkyl, lower-alkyl-C(O)O, CO-lower-alkyl, $CONH_2$, CON(H, lower-alkyl), CON(lower-alkyl)$_2$, lower-alkyl-CO—NH, lower-alkyl-CO—N(lower-alkyl), $NH_2$—CO-lower-alkyl, NH(lower-alkyl)-CO-lower-alkyl, N(lower-alkyl)$_2$-CO-lower-alkyl, $NH_2$, N(H,lower-alkyl), N(lower-alkyl)$_2$, $NH_2$-lower-alkyl, N(H,lower-alkyl)-lower-alkyl, N(lower-alkyl)$_2$-lower-alkyl, cycloalkyl, piperidinyl, piperazinyl and (N-lower-alkyl)-piperazinyl;

$R^2$ is aryl or heteroaryl, each of which is optionally substituted with 1 to 4 substituents independently selected from the group consisting of halogen, cyano, lower-alkyl, lower-alkoxy, fluoro-lower-alkyl, lower-alkinyl, lower-alkyl-$SO_2$, COOH, $CONH_2$, $NH_2$—$SO_2$, COO-lower-alkyl, lower-alkoxy-lower-alkyl, CON(H,lower-alkyl), CON(lower-alkyl)$_2$, N(H,lower-alkyl)-$SO_2$, N(lower-alkyl)$_2$-$SO_2$, lower-alkenyl, hydroxy, $NO_2$, morpholinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), $NH_2$—CO-lower-alkyl, NH(lower-alkyl)-CO-lower-alkyl, N(lower-alkyl)$_2$-CO-lower-alkyl, CO-lower-alkyl, $NH_2$, N(H,lower-alkyl), N(lower-alkyl)$_2$, $NH_2$-lower-alkyl, N(H,lower-alkyl)-lower-alkyl, N(lower-alkyl)$_2$-lower-alkyl, tri(lower-alkyl)silyl-loweralkinyl and cycloalkyl, or wherein two substituents at adjacent positions on the aryl or heteroaryl are bound together to form a ring and said two bound substituents are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

$R^3$ is hydrogen, lower-alkyl, fluoro-lower-alkyl, lower-alkoxy, fluoro-lower-alkoxy, halogen, hydroxy or phenyl; and $R^4$ is hydrogen, lower-alkyl, fluoro-lower-alkyl, lower-alkoxy, fluoro-lower-alkoxy, halogen, hydroxy or phenyl; and pharmaceutically acceptable salts and esters thereof.

Compounds of formula (I) are individually preferred and physiologically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

One embodiment of the present invention provides compounds of formula (I) as defined above, wherein $R^2$ is aryl or heteroaryl, each of which is optionally substituted with 1 to 4 substituents independently selected from the group consisting of halogen, cyano, lower-alkyl, lower-alkoxy, fluoro-lower-alkyl, lower-alkinyl, lower-alkyl-$SO_2$, COOH, $CONH_2$, $NH_2$—$SO_2$, COO-lower-alkyl, lower-alkoxy-lower-alkyl, CON(H,lower-alkyl), CON(lower-alkyl)$_2$, N(H, lower-alkyl)-$SO_2$, N(lower-alkyl)$_2$-$SO_2$, lower-alkenyl, hydroxy, $NO_2$, morpholinyl, piperidinyl, piperazinyl, (N-lower-alkyl)-piperazinyl, pyrrolidinyl, lower-alkyl-C(O) O, lower-alkyl-CO—NH, lower-alkyl-CO—N(lower-alkyl), $NH_2$—CO-lower-alkyl, NH(lower-alkyl)-CO-lower-alkyl, N(lower-alkyl)$_2$-CO-lower-alkyl, CO-lower-alkyl, $NH_2$, N(H,lower-alkyl), N(lower-alkyl)$_2$, $NH_2$-lower-alkyl, N(H, lower-alkyl)-lower-alkyl, N(lower-alkyl)$_2$-lower-alkyl and cycloalkyl, or wherein two substituents at adjacent positions on the aryl or heteroaryl are bound together to form a ring and said two bound substituents are lower-alkylene, dioxo-lower-alkylene, dioxo-fluoro-lower-alyklene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, loweralkylene-N(lower alkyl)-C(O)-lower-alkylene, C(O)—NH-lower-alkylene or C(O)—N(lower-alkyl)-lower-alkylene.

In another embodiment, the present invention provides compounds of formula (I) as described above, wherein $R^1$ is heteroaryl selected from the group consisting of pyridinyl, isoquinolinyl and quinolinyl, which heteroaryl is optionally substituted with 1 to 3 substituents independently selected from the group consisting of lower-alkyl, lower-alkoxy, fluoro-lower-alkyl, fluoro-lower-alkoxy, lower-alkyl-$SO_2$, halogen, cyano, morpholinyl and hydroxy. Particularly, $R^1$ is heteroaryl selected from the group consisting of pyridinyl and quinolinyl, which heteroaryl is optionally substituted with 1 to 2 substituents independently selected from the group consisting of lower-alkyl, fluoro-lower-alkyl, fluoro-lower-alkoxy, lower-alkyl-$SO_2$, halogen, morpholinyl and hydroxy. More particularly, $R^1$ is pyridin-4-yl, 2-chloro-pyridin-4-yl, 2-methansulfonyl-pyridin-4-yl, pyridin-3-yl, 5-methyl-pyridin-3-yl, 2-morpholin-4-yl-pyridin-4-yl, 2-hydroxy-pyridin-4-yl, 5-chloro-pyridin-3-yl, 5-trifluoromethyl-pyridin-3-yl, 5-difluoromethoxy-pyridin-3-yl, 6-trifluoromethyl-pyridin-3-yl, quinolin-3-yl or 2-methyl-pyridin-4-yl.

Other compounds of the present invention are those wherein $R^2$ is aryl selected from the group consisting of phenyl and naphthyl or heteroaryl selected from the group consisting of pyridinyl, quinolinyl and isoquinolinyl, which aryl or heteroaryl is optionally substituted with 1 to 3 substituents independently selected from the group consisting of halogen, cyano, lower-alkyl, fluoro-lower-alkyl, COOH, $NH_2$—$SO_2$, COO-lower-alkyl, N(lower-alkyl)$_2$-$SO_2$, piperazinyl, (N-lower-alkyl)-piperazinyl, lower-alkinyl and tri(lower-alkyl)silyl-loweralkinyl, or wherein two substituents at adjacent positions on the aryl or heteroaryl are bound together to form a ring and said two bound substituents are dioxo-lower-alkylene.

Other compounds of the present invention are those, wherein $R^2$ is aryl selected from the group consisting of phenyl and naphthyl or heteroaryl selected from the group consisting of pyridinyl, quinolinyl and isoquinolinyl, which aryl or heteroaryl is optionally substituted with 1 to 3 substituents independently selected from the group consisting of halogen, cyano, lower-alkyl, fluoro-lower-alkyl, COOH, $NH_2$—$SO_2$, COO-lower-alkyl, N(lower-alkyl)$_2$-$SO_2$, piperazinyl, and (N-lower-alkyl)-piperazinyl, or wherein two substituents at adjacent positions on the aryl or heteroaryl are bound together to form a ring and said two bound substituents are dioxo-lower-alkylene.

Particularly, $R^2$ is aryl selected from the group consisting of phenyl and naphthyl or heteroaryl selected from the group consisting of quinolinyl and isoquinolinyl, which aryl or heteroaryl is optionally substituted with 1 to 2 substituents independently selected from the group consisting of halogen and lower-alkinyl, or wherein two substituents at adjacent positions on the aryl or heteroaryl are bound together to form a ring and said two bound substituents are dioxo-lower-alkylene. It is furthermore preferred that $R^2$ is aryl selected from the group consisting of phenyl and naphthyl or heteroaryl selected from the group consisting of quinolinyl and isoquinolinyl, which aryl or heteroaryl is optionally substituted with 1 to 2 substituents independently selected from the group consisting of halogen, or wherein two substituents at adjacent positions on the aryl or heteroaryl are bound together to form a ring and said two bound substituents are dioxo-lower-alkylene.

Other preferred compounds are those, wherein $R^2$ is napthalen-1-yl, quinolin-4-yl, phenyl, benzo[1,3]dioxol-5-yl, 3-fluoro-phenyl, 2,3-dihydro-benzo[1,4]dioxin-6-yl, 3-chloro-phenyl, 2-fluoro-phenyl, 3-bromo-phenyl, 3-ethy-nyl-phenyl or isoquinolin-5-yl, particularly those, wherein $R^2$ is napthalen-1-yl, quinolin-4-yl, phenyl, benzo[1,3]dioxol-5-yl, 3-fluoro-phenyl, 2,3-dihydro-benzo[1,4]dioxin-6-yl, 3-chloro-phenyl, 2-fluoro-phenyl or isoquinolin-5-yl.

Another embodiment of the present invention provides compounds as defined above, wherein $R^3$ is hydrogen. Other compounds of the present invention are those, wherein $R^4$ is hydrogen.

In particular, compounds of the invention are the compounds of formula (I) described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Preferred compounds of formula (I) are those selected from the group consisting of:

3-[2-(6-Chloro-pyridin-2-yl)-2H-pyrazol-3-yl]-1-pyridin-4-yl-1H-pyridazin-4-one, 1-Pyridin-4-yl-3-(2-pyridin-2-yl-2H-pyrazol-3-yl)-1H-pyridazin-4-one, 3-[5-(4-Oxo-1-pyridin-4-yl-1,4-dihydro-pyridazin-3-yl)-pyrazol-1-yl]-benzonitrile, 3-[2-(2-Fluoro-phenyl)-2H-pyrazol-3-yl]-1-pyridin-4-yl-1H-pyridazin-4-one, 3-[5-(4-Oxo-1-pyridin-4-yl-1,4-dihydro-pyridazin-3-yl)-pyrazol-1-yl]-benzoic acid, 3-[2-(4-Chloro-phenyl)-2H-pyrazol-3-yl]-1-pyridin-4-yl-1H-pyridazin-4-one, 3-[2-(4-Fluoro-phenyl)-2H-pyrazol-3-yl]-1-pyridin-4-yl-1H-pyridazin-4-one, 4-[5-(4-Oxo-1-pyridin-4-yl-1,4-dihydro-pyridazin-3-yl)-pyrazol-1-yl]-benzenesulfonamide, 3-[2-(3,5-Dichloro-pyridin-4-yl)-2H-pyrazol-3-yl]-1-pyridin-4-yl-1H-pyridazin-4-one, 3-[5-(4-Oxo-1-pyridin-4-yl-1,4-dihydro-pyridazin-3-yl)-pyrazol-1-yl]-benzoic acid 1-Pyridin-4-yl-3-(2-p-tolyl-2H-pyrazol-3-yl)-1H-pyridazin-4-one, 3-[2-(2-Chloro-phenyl)-2H-pyrazol-3-yl]-1-pyridin-4-yl-1H-pyridazin-4-one, 1-(2-Chloro-pyridin-4-yl)-3-(2-naphthalen-1-yl-2H-pyrazol-3-yl)-1H-pyridazin-4-one, 3-[2-(2,8-Bis-trifluoromethyl-quinolin-4-yl)-2H-pyrazol-3-yl]-1-pyridin-4-yl-1H-pyridazin-4-one, 3-[2-(2,3-Dihydro-benzo[1,4]dioxin-6-yl)-2H-pyrazol-3-yl]-1-pyridin-4-yl-1H-pyridazin-4-one, 1-(2-Methanesulfonyl-pyridin-4-yl)-3-(2-naphthalen-1-yl-2H-pyrazol-3-yl)-1H-pyridazin-4-one, 3-[2-(2,3-Dihydro-benzo[1,4]dioxin-6-yl)-2H-pyrazol-3-yl]-1-(2-methanesulfonyl-pyridin-4-yl)-1H-pyridazin-4-one, 3-[2-(3-Chloro-phenyl)-2H-pyrazol-3-yl]-1-pyridin-4-yl-1H-pyridazin-4-one, 3-[2-(2-Methyl-pyridin-4-yl)-2H-pyrazol-3-yl]-1-pyridin-4-yl-1H-pyridazin-4-one, 1-Pyridin-4-yl-3-(2-quinolin-4-yl-2H-pyrazol-3-yl)-1H-pyridazin-4-one, 3-(2-Isoquinolin-5-yl-2H-pyrazol-3-yl)-1-pyridin-4-yl-1H-pyridazin-4-one, 1-Pyridin-4-yl-3-(2-quinolin-5-yl-2H-pyrazol-3-yl)-1H-pyridazin-4-one, 3-[2-(2-Chloro-pyridin-4-yl)-2H-pyrazol-3-yl]-1-pyridin-4-yl-1H-pyridazin-4-one, 3-{2-[2-(4-Methyl-piperazin-1-yl)-pyridin-4-yl]-2H-pyrazol-3-yl}-1H-pyridazin-4-one, 3-[2-(2-Piperazin-1-yl-pyridin-4-yl)-2H-pyrazol-3-yl]-1-pyridin-4-yl-1H-pyridazin-4-one,
1-Pyridin-4-yl-3-(2-quinolin-8-yl-2H-pyrazol-3-yl)-1H-pyridazin-4-one,
3-(2-Isoquinolin-8-yl-2H-pyrazol-3-yl)-1-pyridin-4-yl-1H-pyridazin-4-one,
N,N-Dimethyl-3-[5-(4-oxo-1-pyridin-4-yl-1,4-dihydro-pyridazin-3-yl)-pyrazol-1-yl]-benzenesulfonamide,
3-[2-(2,3-Difluoro-phenyl)-2H-pyrazol-3-yl]-1-pyridin-4-yl-1H-pyridazin-4-one,
3-(2-Phenyl-2H-pyrazol-3-yl)-1-pyridin-4-yl-1H-pyridazin-4-one,
1-Pyridin-4-yl-3-(2-pyridin-4-yl-2H-pyrazol-3-yl)-1H-pyridazin-4-one,
3-(2-Benzo[1,3]dioxol-5-yl-2H-pyrazol-3-yl)-1-pyridin-3-yl-1H-pyridazin-4-one,
1-Pyridin-3-yl-3-(2-pyridin-2-yl-2H-pyrazol-3-yl)-1H-pyridazin-4-one,
3-[2-(2,3-Dihydro-benzo[1,4]dioxin-6-yl)-2H-pyrazol-3-yl]-1-pyridin-3-yl-1H-pyridazin-4-one,
3-[2-(3-Fluoro-phenyl)-2H-pyrazol-3-yl]-1-pyridin-3-yl-1H-pyridazin-4-one,
3-[2-(2,3-Dihydro-benzo[1,4]dioxin-6-yl)-2H-pyrazol-3-yl]-1-(5-methyl-pyridin-3-yl)-1H-pyridazin-4-one,
3-[2-(3-Fluoro-phenyl)-2H-pyrazol-3-yl]-1-(5-methyl-pyridin-3-yl)-1H-pyridazin-4-one,
3-[2-(2,3-Dihydro-benzo[1,4]dioxin-6-yl)-2H-pyrazol-3-yl]-1-(2-methyl-pyridin-4-yl)-1H-pyridazin-4-one,
3-[2-(3-Fluoro-phenyl)-2H-pyrazol-3-yl]-1-(2-methyl-pyridin-4-yl)-1H-pyridazin-4-one,
3-[2-(3-Fluoro-phenyl)-2H-pyrazol-3-yl]-1-(2-methoxy-pyridin-4-yl)-1H-pyridazin-4-one,
3-[2-(2,3-Dihydro-benzo[1,4]dioxin-6-yl)-2H-pyrazol-3-yl]-1-(2-morpholin-4-yl-pyridin-4-yl)-1H-pyridazin-4-one,
3-[2-(3-Fluoro-phenyl)-2H-pyrazol-3-yl]-1-(2-morpholin-4-yl-pyridin-4-yl)-1H-pyridazin-4-one,
4-{3-[2-(2,3-Dihydro-benzo[1,4]dioxin-6-yl)-2H-pyrazol-3-yl]-4-oxo-4H-pyridazin-1-yl}-pyridine-2-carbonitrile,
4-{3-[2-(3-Fluoro-phenyl)-2H-pyrazol-3-yl]-4-oxo-4H-pyridazin-1-yl}-pyridine-2-carbonitrile,
3-[2-(3-Fluoro-phenyl)-2H-pyrazol-3-yl]-1-(5-methanesulfonyl-pyridin-3-yl)-1H-pyridazin-4-one,
3-[2-(2,3-Dihydro-benzo[1,4]dioxin-6-yl)-2H-pyrazol-3-yl]-1-(2-hydroxy-pyridin-4-yl)-1H-pyridazin-4-one,
3-[2-(2,5-Difluoro-phenyl)-2H-pyrazol-3-yl]-1-pyridin-3-yl-1H-pyridazin-4-one,
3-[2-(6-Fluoro-quinolin-4-yl)-2H-pyrazol-3-yl]-1-(5-methyl-pyridin-3-yl)-1H-pyridazin-4-one,
1-(5-Fluoro-pyridin-3-yl)-3-[2-(6-fluoro-quinolin-4-yl)-2H-pyrazol-3-yl]-1H-pyridazin-4-one,
3-[2-(6-Fluoro-quinolin-4-yl)-2H-pyrazol-3-yl]-1-pyridin-3-yl-1H-pyridazin-4-one,
1-(5-Chloro-pyridin-3-yl)-3-(2-quinolin-4-yl-2H-pyrazol-3-yl)-1H-pyridazin-4-one,
1-(5-Chloro-pyridin-3-yl)-3-[2-(6-fluoro-quinolin-4-yl)-2H-pyrazol-3-yl]-1H-pyridazin-4-one,
3-[2-(3-Chloro-phenyl)-2H-pyrazol-3-yl]-1-(5-chloro-pyridin-3-yl)-1H-pyridazin-4-one,
1-(2-Chloro-pyridin-4-yl)-3-(2-quinolin-4-yl-2H-pyrazol-3-yl)-1H-pyridazin-4-one,
1-(2-Chloro-pyridin-4-yl)-3-[2-(6-fluoro-quinolin-4-yl)-2H-pyrazol-3-yl]-1H-pyridazin-4-one,
3-[2-(3-Chloro-phenyl)-2H-pyrazol-3-yl]-1-(2-chloro-pyridin-4-yl)-1H-pyridazin-4-one,
1-(2-Chloro-pyridin-4-yl)-3-[2-(2-chloro-pyridin-4-yl)-2H-pyrazol-3-yl]-1H-pyridazin-4-one,
1-(2-Chloro-pyridin-4-yl)-3-(2-quinolin-5-yl-2H-pyrazol-3-yl)-1H-pyridazin-4-one,
1-(2-Chloro-pyridin-4-yl)-3-(2-isoquinolin-5-yl-2H-pyrazol-3-yl)-1H-pyridazin-4-one,
1-(5-Chloro-pyridin-3-yl)-3-(2-quinolin-5-yl-2H-pyrazol-3-yl)-1H-pyridazin-4-one,
1-(5-Chloro-pyridin-3-yl)-3-[2-(6-chloro-quinolin-4-yl)-2H-pyrazol-3-yl]-1H-pyridazin-4-one,
1-(2-Chloro-pyridin-4-yl)-3-[2-(6-chloro-quinolin-4-yl)-2H-pyrazol-3-yl]-1H-pyridazin-4-one,
1-(2-Chloro-pyridin-4-yl)-3-[2-(2-fluoro-phenyl)-2H-pyrazol-3-yl]-1H-pyridazin-4-one,
1-(5-Chloro-pyridin-3-yl)-3-[2-(2-fluoro-phenyl)-2H-pyrazol-3-yl]-1H-pyridazin-4-one,
3-[2-(2-Fluoro-phenyl)-2H-pyrazol-3-yl]-1-isoquinolin-4-yl-1H-pyridazin-4-one,
3-[2-(3-Chloro-phenyl)-2H-pyrazol-3-yl]-1-isoquinolin-4-yl-1H-pyridazin-4-one,
3-[2-(3-Chloro-phenyl)-2H-pyrazol-3-yl]-1-(5-trifluoromethyl-pyridin-3-yl)-1H-pyridazin-4-one,
3-[2-(2-Fluoro-phenyl)-2H-pyrazol-3-yl]-1-(5-trifluoromethyl-pyridin-3-yl)-1H-pyridazin-4-one,
1-(2-Chloro-pyridin-4-yl)-3-[2-(7-chloro-quinolin-4-yl)-2H-pyrazol-3-yl]-1H-pyridazin-4-one,
1-(5-Chloro-pyridin-3-yl)-3-[2-(7-chloro-quinolin-4-yl)-2H-pyrazol-3-yl]-1H-pyridazin-4-one,
3-(2-Quinolin-4-yl-2H-pyrazol-3-yl)-1-(5-trifluoromethyl-pyridin-3-yl)-1H-pyridazin-4-one,
3-[2-(6-Chloro-quinolin-4-yl)-2H-pyrazol-3-yl]-1-pyridin-4-yl-1H-pyridazin-4-one,
3-(2-Isoquinolin-4-yl-2H-pyrazol-3-yl)-1-pyridin-4-yl-1H-pyridazin-4-one,
1-(5-Difluoromethoxy-pyridin-3-yl)-3-[2-(2-fluoro-phenyl)-2H-pyrazol-3-yl]-1H-pyridazin-4-one,
3-[2-(2-Fluoro-phenyl)-2H-pyrazol-3-yl]-1-(6-trifluoromethyl-pyridin-3-yl)-1H-pyridazin-4-one,
5-{3-[2-(2-Fluoro-phenyl)-2H-pyrazol-3-yl]-4-oxo-4H-pyridazin-1-yl}-pyridine-2-carbonitrile,
1-(6-Chloro-pyridin-3-yl)-3-[2-(2-fluoro-phenyl)-2H-pyrazol-3-yl]-1H-pyridazin-4-one,
3-[2-(2-Fluoro-phenyl)-2H-pyrazol-3-yl]-1-quinolin-3-yl-1H-pyridazin-4-one,
1-(2-Methyl-pyridin-4-yl)-3-(2-quinolin-4-yl-2H-pyrazol-3-yl)-1H-pyridazin-4-one,
3-(2-Quinolin-5-yl-2H-pyrazol-3-yl)-1-(6-trifluoromethyl-pyridin-3-yl)-1H-pyridazin-4-one,
3-(2-Isoquinolin-5-yl-2H-pyrazol-3-yl)-1-(6-trifluoromethyl-pyridin-3-yl)-1H-pyridazin-4-one,
3-[2-(7-Chloro-quinolin-4-yl)-2H-pyrazol-3-yl]-1-(5-methyl-pyridin-3-yl)-1H-pyridazin-4-one,
1-(2-Methyl-pyridin-4-yl)-3-(2-quinolin-5-yl-2H-pyrazol-3-yl)-1H-pyridazin-4-one,
1-Pyridin-3-yl-3-(2-quinolin-5-yl-2H-pyrazol-3-yl)-1H-pyridazin-4-one,
3-(2-Isoquinolin-5-yl-2H-pyrazol-3-yl)-1-(2-methyl-pyridin-4-yl)-1H-pyridazin-4-one,
3-(2-Isoquinolin-5-yl-2H-pyrazol-3-yl)-1-pyridin-3-yl-1H-pyridazin-4-one,
5-{3-[2-(2-Fluoro-phenyl)-2H-pyrazol-3-yl]-4-oxo-4H-pyridazin-1-yl}-nicotinonitrile, and
1-(6-Chloro-pyridin-3-yl)-3-[2-(2-methyl-pyridin-4-yl)-2H-pyrazol-3-yl]-1H-pyridazin-4-one,
and pharmaceutically acceptable salts and esters thereof Particularly preferred compounds of formula (I) are those selected from the group consisting of:
1-(2-Chloro-pyridin-4-yl)-3-(2-naphthalen-1-yl-2H-pyrazol-3-yl)-1H-pyridazin-4-one, 1-(2-Methanesulfonyl-pyridin-4-yl)-3-(2-naphthalen-1-yl-2H-pyrazol-3-yl)-1H-pyridazin-4-one,
1-Pyridin-4-yl-3-(2-quinolin-4-yl-2H-pyrazol-3-yl)-1H-pyridazin-4-one,
3-(2-Phenyl-2H-pyrazol-3-yl)-1-pyridin-4-yl-1H-pyridazin-4-one,
3-(2-Benzo[1,3]dioxol-5-yl-2H-pyrazol-3-yl)-1-pyridin-3-yl-1H-pyridazin-4-one,
3-[2-(3-Fluoro-phenyl)-2H-pyrazol-3-yl]-1-(5-methyl-pyridin-3-yl)-1H-pyridazin-4-one,
3-[2-(2,3-Dihydro-benzo[1,4]dioxin-6-yl)-2H-pyrazol-3-yl]-1-(2-morpholin-4-yl-pyridin-4-yl)-1H-pyridazin-4-one,
3-[2-(2,3-Dihydro-benzo[1,4]dioxin-6-yl)-2H-pyrazol-3-yl]-1-(2-hydroxy-pyridin-4-yl)-1H-pyridazin-4-one,
1-(5-Chloro-pyridin-3-yl)-3-(2-quinolin-4-yl-2H-pyrazol-3-yl)-1H-pyridazin-4-one,
3-[2-(3-Chloro-phenyl)-2H-pyrazol-3-yl]-1-(2-chloro-pyridin-4-yl)-1H-pyridazin-4-one,
3-[2-(3-Chloro-phenyl)-2H-pyrazol-3-yl]-1-(5-trifluoromethyl-pyridin-3-yl)-1H-pyridazin-4-one,
1-(5-Difluoromethoxy-pyridin-3-yl)-3-[2-(2-fluoro-phenyl)-2H-pyrazol-3-yl]-1H-pyridazin-4-one,
3-[2-(2-Fluoro-phenyl)-2H-pyrazol-3-yl]-1-(6-trifluoromethyl-pyridin-3-yl)-1H-pyridazin-4-one,
3-[2-(2-Fluoro-phenyl)-2H-pyrazol-3-yl]-1-quinolin-3-yl-1H-pyridazin-4-one,
1-(2-Methyl-pyridin-4-yl)-3-(2-quinolin-4-yl-2H-pyrazol-3-yl)-1H-pyridazin-4-one, and
3-(2-Isoquinolin-5-yl-2H-pyrazol-3-yl)-1-(2-methyl-pyridin-4-yl)-1H-pyridazin-4-one,
and pharmaceutically acceptable salts and esters thereof.

Other preferred compounds of formula (I) are those selected from the group consisting of:
1-(5-Difluoromethoxy-pyridin-3-yl)-3-(2-quinolin-5-yl-2H-pyrazol-3-yl)-1H-pyridazin-4-one,
3-[2-(2-Fluoro-phenyl)-2H-pyrazol-3-yl]-1-(5-methyl-pyridin-3-yl)-1H-pyrazin-4-one,
3-[2-(7-Chloro-quinolin-4-yl)-2H-pyrazol-3-yl]-1-pyridin-4-yl-1H-pyridazin-4-one,
3-[2-(3-Methyl-pyridin-4-yl)-2H-pyrazol-3-yl]-1-pyridin-4-yl-1H-pyridazin-4-one,
3-[2-(2-Fluoro-phenyl)-2H-pyrazol-3-yl]-1-(2-methyl-pyridin-4-yl)-1H-pyridazin-4-one,
3-[2-(2-Fluoro-phenyl)-2H-pyrazol-3-yl]-1-(2-trifluoromethyl-pyridin-4-yl)-1H-pyridazin-4-one,
3-[2-(3-Chloro-phenyl)-2H-pyrazol-3-yl]-1-(2-trifluoromethyl-pyridin-4-yl)-1H-pyridazin-4-one,
4-{3-[2-(2-Fluoro-phenyl)-2H-pyrazol-3-yl]-4-oxo-4H-pyridazin-1-yl}-pyridine-2-carbonitrile,
3-[2-(3-Bromo-phenyl)-2H-pyrazol-3-yl]-1-pyridin-4-yl-1H-pyridazin-4-one,
1-Pyridin-4-yl-3-[2-(3-trimethylsilanylethynyl-phenyl)-2H-pyrazol-3-yl]-1H-pyridazin-4-one,
3-[2-(3-Ethynyl-phenyl)-2H-pyrazol-3-yl]-1-pyridin-4-yl-1H-pyridazin-4-one,
3-[2-(2-Fluoro-phenyl)-2H-pyrazol-3-yl]-1-isoquinolin-6-yl-1H-pyridazin-4-one,
3-[2-(3-Fluoro-phenyl)-2H-pyrazol-3-yl]-1-isoquinolin-6-yl-1H-pyridazin-4-one,
3-[2-(2-Fluoro-phenyl)-2H-pyrazol-3-yl]-1-quinolin-6-yl-1H-pyridazin-4-one, and
3-[2-(3-Chloro-phenyl)-2H-pyrazol-3-yl]-1-quinolin-6-yl-1H-pyridazin-4-one
and pharmaceutically acceptable salts and esters thereof.

Other particularly preferred compounds of formula (I) are those selected from the group consisting of:
3-[2-(3-Bromo-phenyl)-2H-pyrazol-3-yl]-1-pyridin-4-yl-1H-pyridazin-4-one, and
3-[2-(3-Ethynyl-phenyl)-2H-pyrazol-3-yl]-1-pyridin-4-yl-1H-pyridazin-4-one
and pharmaceutically acceptable salts and esters thereof It will be appreciated that the compounds of formula (I) in this invention can be derivatized at functional groups to provide derivatives which are capable of conversion back to the parent compound in vivo.

The invention further provides a process for the manufacture of compounds of formula (I) as defined above, which process comprises reacting a compound of formula (II)

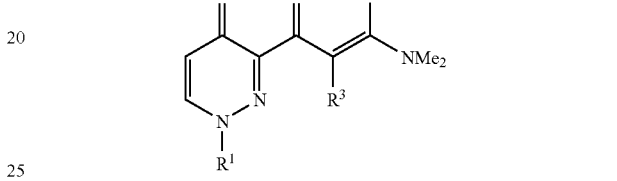

with a compound of the formula $R^2$—NH—$NH_2$, wherein $R^1$, $R^2$, $R^3$ and $R^4$ are as defined above.

The reaction of a compound of formula (II) with a compound of the formula $R^2$—NH—$NH_2$ can be carried out under conditions as described in the examples or under conditions well known to the person skilled in the art. For example, the reaction can be performed in solvents like DMF, acetic acid, ethanol, water, a mixture of ethanol with hydrochloric acid and the like at elevated temperatures, e.g. at 100-200° C., at atmospheric pressure or elevated pressure. The reaction can be performed at the reflux temperature of the respective solvent, or it can be performed at temperatures above boiling point by applying sealed tubes and using microwave irradiation conditions.

The present invention also provides compounds of formula (I) as defined above, when prepared by a process as described above.

The compounds of formula (II) and $R^2$—NH—$NH_2$, can be prepared by methods known in the art or as described below or in analogy thereto. Unless otherwise indicated, $R^1$, $R^2$, $R^3$, and $R^4$ are as described above.

The pyridazinones of formula (I) can be prepared starting from anilines of formula 2 (see scheme 1 below). Anilines 2 are either commercially available or can be prepared from commercial precursors as e.g. from their corresponding nitro compounds by reductive methods. Another option is to convert commercial anilines into the desired anilines 2 by standard methods known in the art. Conversion of anilines 2 into their corresponding diazonium salts of formula 3 can be done using standard methods known to those skilled in the art as e.g. treatment of the aniline in a mineral acid as e.g. hydrochloric acid, sulfuric acid or phosphoric acid with sodium nitrite. The formed diazonium salts 3 can be used without any further purification for the condensation with suitable 1,3-diketones 4 resulting in diazo compounds of formula 5. This reaction is preferentially performed in an alcohol/water mixture at low temperatures (0-5° C.) at almost neutral pH value (pH 5-6) which can be achieved by adding suitable basic salts like e.g. ammonium acetate. The diazo compounds of formula 5 can tautomerize to the corresponding hydrazones.

The pyridazin-4-one ring can be formed by reacting the intermediate diazo compounds of formula 5 with C1-equivalents like e.g. formaldehyde, N,N-dimethylformamide or N,N-dimethylformamide dimethyl acetal. The reaction with N,N-dimethylformamide dimethyl acetal affords the pyridazinone intermediates of formula 6 bearing a 1,3-diketone equivalent as side chain.

The side chain 1,3-diketone equivalent of pyridazinones 6 is used to form the final products of formula (I) by condensing pyridazinones 6 with suitable hydrazines of formula 7. This reaction is usually performed in solvents like DMF, acetic acid, ethanol, water, a mixture of ethanol with hydrochloric acid and the like at elevated temperatures. The reaction can be performed at the reflux temperature of the respective solvent, or it can be performed at temperatures above boiling point by applying sealed tubes and using microwave irradiation conditions.

Hydrazines of formula 7 are commercially available or can be prepared by methods known to those skilled in the art. Straightforward synthetic methods starting from commercial precursors include the conversion of the corresponding anilines with sodium nitrite and tin-(II)-chloride and the treatment of hydrazine hydrate with aromatic/heteroaromatic halides.

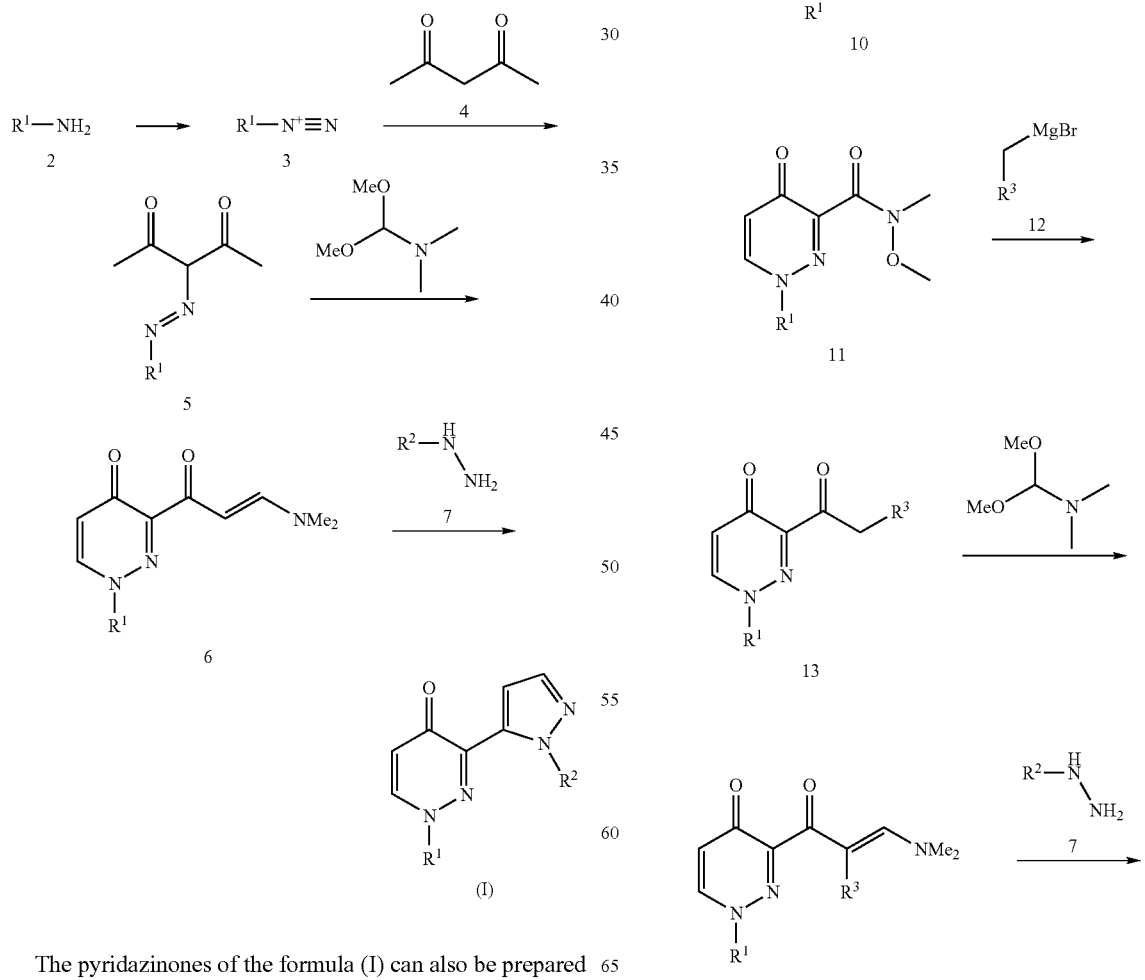

The pyridazinones of the formula (I) can also be prepared starting from anilines of formula 2 according to scheme 2 (see below).

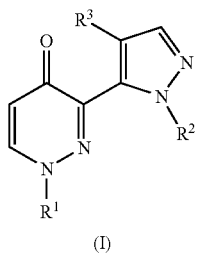

(I)

Conversion of anilines 2 into their corresponding diazonium salts of formula 3 can be done as described above. The formed diazonium salts 3 can be used without any further purification for the condensation with suitable ketoesters 8 resulting in diazo compounds of formula 9. This reaction is preferentially performed in an alcohol/water mixture at low temperatures (0-5° C.) at almost neutral pH value (pH 5-6) which can be achieved by adding suitable basic salts like e.g. ammonium acetate. The diazo compounds of formula 9 can tautomerize to the corresponding hydrazones.

The pyridazin-4-one ring can be formed by reacting the intermediate diazo compounds of formula 9 with $C_1$-equivalents like e.g. formaldehyde, N,N-dimethylformamide or N,N-dimethylformamide dimethyl acetal. The reaction with N,N-dimethylformamide dimethyl acetal affords the pyridazinone intermediates of formula 10 bearing an ester equivalent as side chain.

The ester side chain equivalent of pyridazinones 10 can be converted into a ketone most conveniently by functionalization into a suitable activated species such as a Weinreb amide 11, which is disposed towards displacement with an organometalic species, most commonly a Grignard reagent of formula 12 in e.g. a non protic solvent, such as THF or hexane, to give the corresponding ketone 13. This can be again reacted with $C_1$-equivalents like e.g. formaldehyde, N,N-dimethylformamide or N,N-dimethylformamide dimethyl acetal. The reaction with N,N-dimethylformamide dimethyl acetal affords the diketone equivalent of formula 14 which is used to form the final products of formula (I) by condensing with suitable hydrazines of formula 7. This reaction is usually performed in solvents like DMF, acetic acid, ethanol, water, a mixture of ethanol with hydrochloric acid at elevated temperatures. The reaction can be performed at the reflux temperature of the respective solvent, or it can be performed at temperatures above boiling point by applying sealed tubes and using microwave irradiation conditions.

Hydrazines of formula 7 are commercially available or can be prepared by methods known to those skilled in the art. Straightforward synthetic methods starting from commercial precursors include the conversion of the corresponding anilines with sodium nitrite and tin-(II)-chloride and the treatment of hydrazine hydrate with aromatic/heteroaromatic halides.

Certain substituents on the groups $R^1$, $R^2$, $R^3$, and $R^4$ may not be inert to the conditions of the synthesis sequences described above and may require protection by standard protecting groups known in the art. For instance, an amino or hydroxyl group can be protected as an acetyl or tert.-butoxycarbonyl derivative. Alternatively, some substituents can be derived from others at the end of the reaction sequence. For instance, a compound of formula I can be synthesized bearing a nitro-, an ethoxycarbonyl, an ether, a sulfonic acid substituent on the groups $R^1$, $R^2$, $R^3$, and $R^4$, which substituents are finally converted to an amino- (e.g. by reduction of a nitro group or cleavage of a suitable amino protective group (e.g. removal of a Boc group with TFA)), alkylamino- (e.g. by reductive amination of an amino group), dialkylamino- (e.g. by alkylation of an amino group, reduction of an appropriate acylamino group with lithium aluminum hydride or Eschweiler-Clarke reaction with an appropriate amino or alkylamino group), acylamino- (by amide formation from an amino group e.g. with appropriate acyl halides or with appropriate carboxylic acids after their activation with CDI, EDC etc.), alkylsulfonylamino (e.g. by reaction of an amino group with sulfonyl chlorides), arylsulfonylamino substituent (e.g. by reaction of an amino group with sulfonyl chlorides), hydroxyl- (by cleavage of a suitable hydroxy protective group (e.g. hydrogenolytic removal of a benzyl ether or oxidative cleavage of a p-methoxy benzyl ether), ether- (e.g. by Williamson's ether synthesis from a hydroxyl group) or to a carboxamide substituent (e.g. by amide formation from a carboxylic acid group with appropriate amines after activation of the carboxylic acid group with CDI, EDC etc. or conversion to an acyl chloride), or to a sulfonamide substituent by standard procedures.

The corresponding salts with acids can be obtained by standard methods known to the person skilled in the art, e.g. by dissolving the compound of formula (I) in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention inhibit PDE10A activity. The compounds of the present invention can therefore be used, either alone or in combination with other drugs, for the treatment and/or prophylaxis of diseases which are modulated by PDE10A inhibitors. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive/compulsive disorders, acute stress disorder or generalized anxiety disorder, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Other disorders are diabetes and related disorders, such as type 2 diabetes mellitus, neurodegenerative disorders such as Alzheimer's disease, Huntington's disease, Parkinson's disease, multiple sclerosis, stroke or spinal cord injury, solid tumors and hematological malignancies such as renal cell carcinoma or breast cancer.

The invention therefore also provides pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by PDE10A inhibitors, particularly as therapeutically active substances for the treatment and/or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

In another preferred embodiment, the invention provides a method for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, which method comprises administering a compound as defined above to a human being or animal.

The invention also embraces the use of compounds as defined above for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

The invention also provides the use of compounds as described above for the preparation of medicaments for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer. Such medicaments comprise a compound as described above.

Prevention and/or treatment of schizophrenia is a preferred indication. Furthermore, prevention and/or treatment of positive, negative and/or cognitive symptoms associated with schizophrenia is preferred.

The following tests were carried out in order to determine the activity of the compounds of the present invention. PDE10 activity of the compounds of the present invention is determined using a Scintillation Proximity Assay (SPA)-based method similar to the one previously described (Fawcett, L. et al., ProcNatl Acad Sci USA (2000) 97(7):3702-3707).

PDE10A1 and PDE10A2 are two splice variants of PDE10A. There are these 2 splice variants known, which differ in the N-terminal part of the protein. The catalytic domains of PDE10A1 and PDE10A2 are identical. The assay for PDE10A2 described below is therefore also representative for PDE10A1 and also for PDE10A in general.

The PDE10A2 assay was performed in a two step procedure in 96-well micro titer plates. The reaction mixture of 80 µl contained 20 mM HEPES/10 mM $MgCl_2$/0.05 mg/ml buffer (pH 7.5), 50 nM cGMP (Sigma) and 50 nM [$^3$H]-cGMP (GE Healthcare), 0.25 nM PDE10A2 with or without a specific test compound. A range of concentrations of the potential inhibitor was used to generate data for calculating the concentration of inhibitor resulting in 50% of the effect (e.g. $IC_{50}$, the concentration of the competitor inhibiting PDE10A2 activity 50%). Non-specific activity was tested without the enzyme. The reaction was initiated by addition of the substrate solution (cGMP and [$^3$H]-cGMP) and allowed to progress for 30 minutes at room temperature. The reaction was terminated by transferring 50 µl of the reaction mixture into an OptiPlate (Perkin Elmer) containing 25 µl of YSi-SPA scintillation beads (GE Healthcare) in 18 mM zinc sulphate solution (stop reagent). After 1 h under shaking, the plate was centrifuged one minute at 1000 rpm to allow beads to settle. Afterwards, radioactive counts were measured on a Perkin Elmer TopCount Scintillation plate reader.

The catalytic domain of human PDE10A2, residues serine 449 to aspartate 789, was amplified by PCR using cDNA (Origene) and the oligonucleotides 5'-GGGGA- CAAGTTTGT ACAAAAAAGCAGGCTTAGTACCTA-GAGGATCAAGCA*TTTGTACTTCAGAAG*-3' (with AttB1 recombination site in bold and thrombin protease cleavage site in italics) and 5'-GGGGACCACTTTGTACAA-GAAAGCTGGGTCAATCTTCAGATGCAGCTG-3' (with AttB2 recombination site in bold) which conferred Gateway recombination sites. The PCR product was used in a BP recombination reaction with pDONR221 to generate pENTR Thm-PDE10A2(S449-D789) which was DNA sequence verified and then used in an LR recombination reaction with a Gateway modified version of pET11a. The resulting expression vector, placT7.2H6-(gwl)-Thm-PDE10A2(S449-D789) was DNA sequence confirmed and transformed into *E. coli* strain BL21(DE3) pLysS and recombinant protein was produced in TB medium at 20° C. by induction to a final IPTG concentration of 0.5 mM at an optical density of 1.0 at 600 nm for 20 hours. About 30% of the protein was in the soluble fraction of the cell homogenate. The protein was purified using sequential chromatography on Ni-NTA and HiTrapQ/HiTrapS. After thrombin digest at room temperature a HiTrapChelating/HiTrap Benzamindin chromatography removed impurities, uncleaved protein and thrombin. Final purification of PDE10A2(S449-D789) was performed on a Superdex 75 size exclusion chromatography equilibrated with 25 mM HEPES pH 8.4, 0.15 M NaCl. The yield of pure protein was 2 mg/liter of culture volume is relatively low. The purity of the protein was >95%, monomeric and monodisperse as shown by SDS-PAGE, HPLC and analytical ultracentrifugation.

The compounds according to formula (I) preferably have an $IC_{50}$ value below 10 µM, preferably below 5 µM, more preferably below 1 µM. Preferably, the $IC_{50}$ values are above 0.01 nM, more preferable above 0.1 nM, more preferably above 1 nM. The following table shows data for some examples.

| Example | PDE10A2 inhibition $IC_{50}$ [µmol/l] |
|---|---|
| 1 | 8.098 |
| 2 | 10.000 |
| 3 | 0.319 |
| 4 | 0.115 |
| 5 | 0.899 |
| 6 | 0.188 |
| 7 | 0.183 |
| 8 | 6.333 |
| 9 | 10.000 |
| 10 | 0.048 |
| 11 | 0.103 |
| 12 | 0.228 |
| 13 | 0.011 |
| 14 | 10.000 |
| 15 | 0.080 |
| 16 | 0.015 |
| 17 | 0.096 |
| 18 | 0.140 |
| 19 | 0.417 |
| 20 | 0.009 |
| 21 | 0.028 |
| 22 | 0.035 |
| 23 | 1.211 |
| 24 | 10.000 |
| 25 | 10.000 |
| 26 | 0.806 |
| 27 | 0.126 |
| 28 | 3.225 |
| 29 | 0.219 |
| 30 | 0.069 |
| 31 | 0.811 |
| 32 | 0.150 |
| 33 | 2.939 |
| 34 | 0.081 |
| 35 | 0.285 |
| 36 | 0.071 |
| 37 | 0.149 |
| 38 | 0.437 |
| 39 | 2.556 |
| 40 | 0.414 |
| 41 | 0.082 |
| 42 | 1.423 |
| 43 | 0.663 |
| 44 | 2.290 |
| 45 | 0.259 |
| 46 | 0.057 |
| 47 | 0.352 |
| 48 | 0.025 |
| 49 | 0.163 |
| 50 | 0.087 |
| 51 | 0.020 |
| 52 | 0.177 |
| 53 | 0.065 |
| 54 | 0.066 |
| 55 | 0.122 |
| 56 | 0.050 |
| 57 | 1.544 |
| 58 | 0.089 |
| 59 | 0.220 |
| 60 | 0.078 |
| 61 | 0.220 |
| 62 | 0.154 |
| 63 | 0.078 |
| 64 | 0.148 |
| 65 | 0.144 |
| 66 | 0.100 |
| 67 | 0.056 |
| 68 | 0.178 |
| 69 | 0.057 |
| 70 | 0.253 |
| 71 | 0.056 |
| 72 | 0.078 |
| 73 | 0.188 |
| 74 | 0.027 |
| 75 | 0.120 |
| 76 | 0.619 |
| 77 | 0.183 |
| 78 | 0.038 |
| 79 | 0.012 |
| 80 | 0.072 |
| 81 | 0.107 |
| 82 | 0.102 |
| 83 | 0.134 |
| 84 | 0.169 |
| 85 | 0.046 |
| 86 | 0.050 |
| 87 | 0.477 |
| 88 | 1.128 |
| 89 | 0.046 |
| 90 | 0.090 |
| 91 | 0.032 |
| 93 | 0.206 |
| 94 | 0.281 |
| 95 | 0.073 |
| 96 | 0.308 |
| 97 | 0.017 |
| 99 | 0.018 |
| 100 | 0.031 |
| 101 | 0.041 |
| 102 | 0.020 |
| 103 | 0.007 |

The compounds of formula (I) and/or their pharmaceutically acceptable salts can be used as medicaments, e.g. in the form of pharmaceutical compositions for enteral, parenteral or topical administration. They can be administered, for example, perorally, e.g. in the form of tablets, coated tablets, dragées, hard and soft gelatin capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The present invention also provides a method for the manufacture of pharmaceutical compositions. Such process comprises bringing one or more compounds of formula (I) and/or their pharmaceutically acceptable salts thereof and, if desired one or more other therapeutically valuable substance, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical compositions are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage at which compounds of formula (I) can be administered can vary within wide limits depending on the disease to be controlled, the age and the individual condition of the patient and the mode of administration, and will, of course, be fitted to the individual requirements in each particular case. For adult patients a daily dosage of about 0.1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 0.1-500 mg, preferably 1-200 mg, of a compound of formula (I).

The following examples serve to illustrate the present invention in more detail. They are, however, not intended to limit its scope in any manner.

EXAMPLES

A. Starting Materials and Intermediates

A-1. Preparation of 3-((E)-3-Dimethylamino-acryloyl)-1-pyridin-4-yl-1H-pyridazin-4-one a) 3-(Pyridin-4-ylazo)-pentane-2,4-dione A solution of pyridine-4-ylamine (4.5 g, 47.81 mmol) in 85% phosphoric acid (30 ml) and 65% nitric acid (20 ml) was cooled to −10° C. and treated with solid sodium nitrite (3.3 g, 47.8 mmol) over 20 mins. Ice (50 g) was added and the mixture added at 0° C. to a suspension of 2,4-pentadione (4.79 g; 47.8 mmol) and potassium acetate (40 g) in EtOH (280 ml). After completion, 20% aq. $Na_2CO_3$ (300 ml) was added at 0° C. until pH reached 7 and the solution extracted with dichloromethane (3×400 ml), dried, concentrated and chromatographed on silica gel with dichloromethane/methanol to give the product as a yellow solid (5.3 g, 54%).

MS: M=206.1 $(M+H)^+$ b) 3-((E)-3-Dimethylamino-acryloyl)-1-pyridin-4-yl-1H-pyridazin-4-one 3-(Pyridin-4-ylazo)-pentane-2,4-dione (2.3 g; 11.2 mmol) was dissolved in N,N-dimethylformamide dimethyl acetal (16 ml) and heated at 100° C. for 60 min. After concentration, the oily crude product was purified by flash chromatography on silica gel (eluent: dichloromethane/methanol) yielding 1.68 g (55%) of A-1 as an orange solid.

MS: M=271.2 $(M+H)^+$

In analogy to the method described above for the synthesis of A-1, the following intermediates were prepared:

| Intermediate | Intermediate name | Amine | MS $(M+H)^+$ |
|---|---|---|---|
| A-2 | 1-(2-Chloro-pyridin-4-yl)-3-((E)-3-dimethylamino-acryloyl)-1H-pyridazin-4-one | 2-Chloro-pyridin-4-ylamine | 305.1 |
| A-3 | 3-((E)-3-Dimethylamino-acryloyl)-1-(2-methanesulfonyl-pyridin-4-yl)-1H-pyridazin-4-one | 2-Methanesulfonyl-pyridin-4-ylamine | 349.1 |
| A-4 | 3-((E)-3-Dimethylamino-acryloyl)-1-pyridin-3-yl-1H-pyridazin-4-one | Pyridin-3-ylamine | 271.4 |
| A-5 | 3-((E)-3-Dimethylamino-acryloyl)-1-(5-methyl-pyridin-3-yl)-1H-pyridazin-4-one | 5-Methyl-pyridin-3-ylamine | 285.3 |
| A-6 | 3-((E)-3-Dimethylamino-acryloyl)-1-(2-methyl-pyridin-4-yl)-1H-pyridazin-4-one | 2-Methyl-pyridin-4-ylamine | 285.3 |
| A-7 | 3-((E)-3-Dimethylamino-acryloyl)-1-(2-methoxy-pyridin-4-yl)-1H-pyridazin-4-one | 2-Methoxy-pyridin-4-ylamine | 301.3 |
| A-8 | 3-((E)-3-Dimethylamino-acryloyl)-1-(2-morpholin-4-yl-pyridin-4-yl)-1H-pyridazin-4-one | 2-Morpholin-4-yl-pyridin-4-ylamine | 356.2 |
| A-9 | 4-[3-((E)-3-Dimethylamino-acryloyl)-4-oxo-4H-pyridazin-1-yl]-pyridine-2-carbonitrile | 4-Amino-pyridine-2-carbonitrile | 296.3 |

-continued

| Intermediate | Intermediate name | Amine | MS (M + H)+ |
|---|---|---|---|
| A-10 | 3-((E)-3-Dimethylamino-acryloyl)-1-(5-methanesulfonyl-pyridin-3-yl)-1H-pyridazin-4-one | 5-Methanesulfonyl-pyridin-3-ylamine | 349.2 |
| A-11 | 3-((E)-3-Dimethylamino-acryloyl)-1-(5-fluoro-pyridin-3-yl)-1H-pyridazin-4-one | 5-Fluoro-pyridin-3-ylamine | 289.2 |
| A-12 | 1-(5-Chloro-pyridin-3-yl)-3-((E)-3-dimethylamino-acryloyl)-1H-pyridazin-4-one | 5-Chloro-pyridin-3-ylamine | 305.1 |
| A-13 | 3-((E)-3-Dimethylamino-acryloyl)-1-isoquinolin-4-yl-1H-pyridazin-4-one | Isoquinolin-4-ylamine | 321.2 |
| A-14 | 3-((E)-3-Dimethylamino-acryloyl)-1-(5-trifluoromethyl-pyridin-3-yl)-1H-pyridazin-4-one | 5-Trifluoromethyl-pyridin-3-ylamine | 339.3 |
| A-15 | 1-(5-Difluoromethoxy-pyridin-3-yl)-3-((E)-3-dimethylamino-acryloyl)-1H-pyridazin-4-one | 5-Difluoromethoxy-pyridin-3-ylamine | 337.3 |
| A-16 | 3-((E)-3-Dimethylamino-acryloyl)-1-(6-trifluoromethyl-pyridin-3-yl)-1H-pyridazin-4-one | 6-Trifluoromethyl-pyridin-3-ylamine | 339.1 |
| A-17 | 5-[3-((E)-3-Dimethylamino-acryloyl)-4-oxo-4H-pyridazin-1-yl]-pyridine-2-carbonitrile | 5-Amino-pyridine-2-carbonitrile | 296.2 |
| A-18 | 1-(6-Chloro-pyridin-3-yl)-3-((E)-3-dimethylamino-acryloyl)-1H-pyridazin-4-one | 6-Chloro-pyridin-3-ylamine | 305.1 |
| A-19 | 3-((E)-3-Dimethylamino-acryloyl)-1-quinolin-3-yl-1H-pyridazin-4-one | Quinolin-3-ylamine | 321.2 |
| A-20 | 5-[3-((E)-3-Dimethylamino-acryloyl)-4-oxo-4H-pyridazin-1-yl]-nicotinonitrile | 5-Amino-nicotinonitrile | 296.2 |
| A-21 | 3-((E)-3-Dimethylamino-acryloyl)-1-(2-trifluoromethyl-pyridin-4-yl)-1H-pyridazin-4-one | 2-Trifluoromethyl-pyridine-4-ylamine | 339.3 |
| A-22 | 3-((E)-3-Dimethylamino-acryloyl)-1-isoquinolin-6-yl-1H-pyridazin-4-one | 6-Aminoisoquinoline | 321.2 |
| A-23 | 3-((E)-3-Dimethylamino-acryloyl)-1-quinolin-6-yl-1H-pyridazin-4-one | 6-Aminoquinoline | 321.2 |

B. Final Products

Example 1

3-[2-(6-Chloro-pyridin-2-yl)-2H-pyrazol-3-yl]-1-pyridin-4-yl-1H-pyridazin-4-one

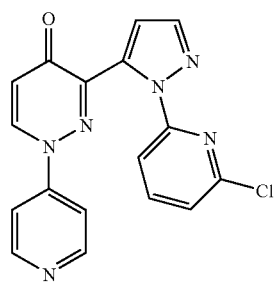 [SMILES: O=c1ccn(-c2ccncc2)nc1-c1ccnn1-c1cccc(Cl)n1]

A solution of 3-((E)-3-dimethylamino-acryloyl)-1-pyridin-4-yl-1H-pyridazin-4-one (A-1; 0.075 g; 0.3 mmol) in EtOH (2 ml) was treated with (6-chloropyridin-2-yl)-hydrazine (0.048 g; 0.3 mmol) in a sealed tube and irradiated at 100° C. for 30 min. Acetic acid (0.5 ml) was added and the mixture again irradiated at 100° C. for 15 min. The solvent of the reaction mixture was removed and the crude product purified by preparative HPLC yielding 0.0122 g (12%) of the final product. MS: M=351.1 (M+H)⁻

Example 2

1-Pyridin-4-yl-3-(2-pyridin-2-yl-2H-pyrazol-3-yl)-1H-pyridazin-4-one

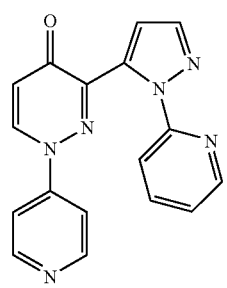 [SMILES: O=c1ccn(-c2ccncc2)nc1-c1ccnn1-c1ccccn1]

1-Pyridin-4-yl-3-(2-pyridin-2-yl-2H-pyrazol-3-yl)-1H-pyridazin-4-one was obtained in analogy to the method of example 1 from intermediate A-1 and pyridin-2-yl-hydrazine. MS: M=371.1 (M+H)+

Example 3

3-[5-(4-Oxo-1-pyridin-4-yl-1,4-dihydro-pyridazin-3-yl)-pyrazol-1-yl]-benzonitrile

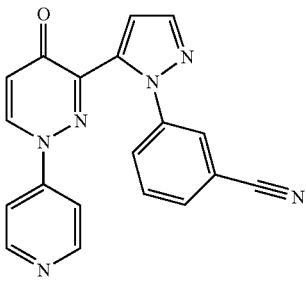 [SMILES: N#Cc1cccc(-n2nccc2-c2nn(-c3ccncc3)ccc2=O)c1]

3-[5-(4-Oxo-1-pyridin-4-yl-1,4-dihydro-pyridazin-3-yl)-pyrazol-1-yl]-benzonitrile was obtained in analogy to the method of example 1 from intermediate A-1 and 3-hydrazino-benzonitrile. MS: M=341.1 (M+H)$^+$

Example 4

3-[2-(2-Fluoro-phenyl)-2H-pyrazol-3-yl]-1-pyridin-4-yl-1H-pyridazin-4-one

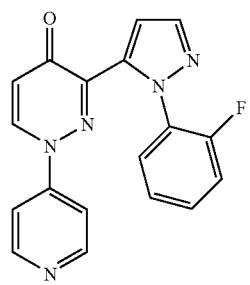 [SMILES: O=c1ccn(-c2ccncc2)nc1-c1ccnn1-c1ccccc1F]

3-[2-(2-Fluoro-phenyl)-2H-pyrazol-3-yl]-1-pyridin-4-yl-1H-pyridazin-4-one was obtained in analogy to the method of example 1 from intermediate A-1 and 2-fluoro-phenylhydrazine. MS: M=334.0 (M+H)$^+$

Example 5

3-[5-(4-Oxo-1-pyridin-4-yl-1,4-dihydro-pyridazin-3-yl)-pyrazol-1-yl]-benzoic acid

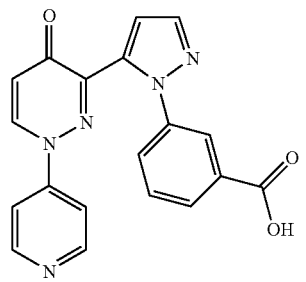 [SMILES: O=C(O)c1cccc(-n2nccc2-c2nn(-c3ccncc3)ccc2=O)c1]

3-[5-(4-Oxo-1-pyridin-4-yl-1,4-dihydro-pyridazin-3-yl)-pyrazol-1-yl]-benzoic acid was obtained in analogy to the method of example 1 from intermediate A-1 and 3-hydrazino-benzoic acid. MS: M=359.8 (M+H)$^+$

Example 6

3-[2-(4-Chloro-phenyl)-2H-pyrazol-3-yl]-1-pyridin-4-yl-1H-pyridazin-4-one

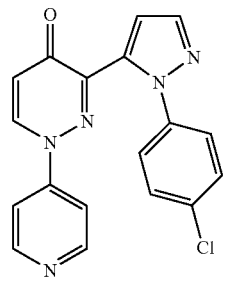 [SMILES: O=c1ccn(-c2ccncc2)nc1-c1ccnn1-c1ccc(Cl)cc1]

3-[2-(4-Chloro-phenyl)-2H-pyrazol-3-yl]-1-pyridin-4-yl-1H-pyridazin-4-one was obtained in analogy to the method of example 1 from intermediate A-1 and 4-chloro-phenylhydrazine. MS: M=349.9 (M+H)$^+$

Example 7

3-[2-(4-Fluoro-phenyl)-2H-pyrazol-3-yl]-1-pyridin-4-yl-1H-pyridazin-4-one

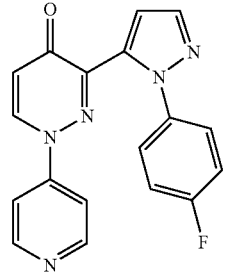 [SMILES: O=c1ccn(-c2ccncc2)nc1-c1ccnn1-c1ccc(F)cc1]

3-[2-(4-Fluoro-phenyl)-2H-pyrazol-3-yl]-1-pyridin-4-yl-1H-pyridazin-4-one was obtained in analogy to the method of example 1 from intermediate A-1 and 4-fluoro-phenylhydrazine. MS: M=334.0 (M+H)$^+$

Example 8

4-[5-(4-Oxo-1-pyridin-4-yl-1,4-dihydro-pyridazin-3-yl)-pyrazol-1-yl]-benzenesulfonamide

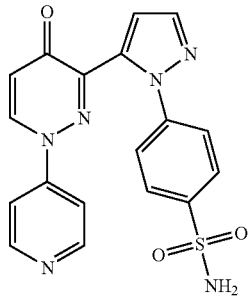 [SMILES: NS(=O)(=O)c1ccc(-n2nccc2-c2nn(-c3ccncc3)ccc2=O)cc1]

4-[5-(4-Oxo-1-pyridin-4-yl-1,4-dihydro-pyridazin-3-yl)-pyrazol-1-yl]-benzenesulfonamide was obtained in analogy to the method of example 1 from intermediate A-1 and 4-hydrazino-benzenesulfonamide. MS: M=395.0 (M+H)+

Example 9

3-[2-(3,5-Dichloro-pyridin-4-yl)-2H-pyrazol-3-yl]-1-pyridin-4-yl-1H-pyridazin-4-one

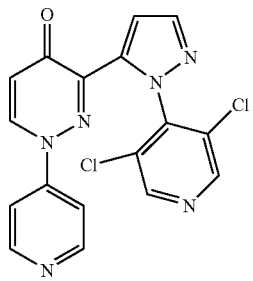 [SMILES: O=c1ccn(-c2ccncc2)nc1-c1ccnn1-c1c(Cl)cncc1Cl]

3-[2-(3,5-Dichloro-pyridin-4-yl)-2H-pyrazol-3-yl]-1-pyridin-4-yl-1H-pyridazin-4-one was obtained in analogy to the method of example 1 from intermediate A-1 and (3,5-dichloropyridin-4-yl)-hydrazine. MS: M=386.7 (M+H)+

Example 10

3-[5-(4-Oxo-1-pyridin-4-yl-1,4-dihydro-pyridazin-3-yl)-pyrazol-1-yl]-benzoic acid methyl ester

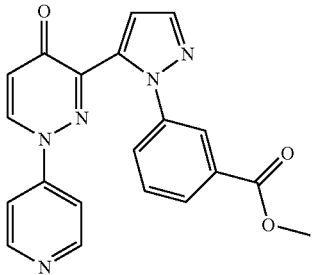 [SMILES: COC(=O)c1cccc(-n2nccc2-c2nn(-c3ccncc3)ccc2=O)c1]

3-[5-(4-Oxo-1-pyridin-4-yl-1,4-dihydro-pyridazin-3-yl)-pyrazol-1-yl]-benzoic acid methyl ester was obtained in analogy to the method of example 1 from intermediate A-1 and 3-hydrazino-benzoic acid methyl ester. MS: M=374.0 (M+H)+

Example 11

1-Pyridin-4-yl-3-(2-p-tolyl-2H-pyrazol-3-yl)-1H-pyridazin-4-one

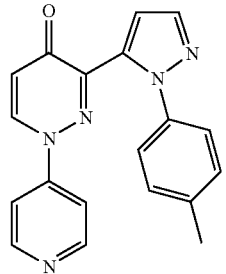 [SMILES: Cc1ccc(-n2nccc2-c2nn(-c3ccncc3)ccc2=O)cc1]

Pyridin-4-yl-3-(2-p-tolyl-2H-pyrazol-3-yl)-1H-pyridazin-4-one was obtained in an to the method of example 1 from intermediate A-1 and 4-methyl-phenylhydrazine. MS: M=330.1 (M+H)+

Example 12

3-[2-(2-Chloro-phenyl)-2H-pyrazol-3-yl]-1-pyridin-4-yl-1H-pyridazin-4-one

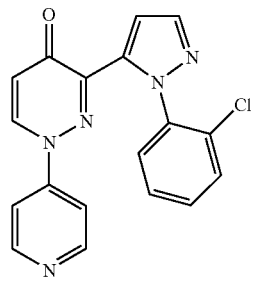 [SMILES: O=c1ccn(-c2ccncc2)nc1-c1ccnn1-c1ccccc1Cl]

3-[2-(2-Chloro-phenyl)-2H-pyrazol-3-yl]-1-pyridin-4-yl-1H-pyridazin-4-one was obtained in analogy to the method of example 1 from intermediate A-1 and 2-chloro-phenylhydrazine. MS: M=349.9 (M+H)+

Example 13

1-(2-Chloro-pyridin-4-yl)-3-(2-naphthalen-1-yl-2H-pyrazol-3-yl)-1H-pyridazin-4-one

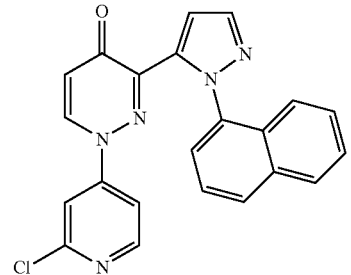 [SMILES: O=c1ccn(-c2ccnc(Cl)c2)nc1-c1ccnn1-c1cccc2ccccc12]

1-(2-Chloro-pyridin-4-yl)-3-(2-naphthalen-1-yl-2H-pyrazol-3-yl)-1H-pyridazin-4-one was obtained in analogy to the method of example 1 from intermediate A-2 and naphthalen-1-yl-hydrazine. MS: M=400.1 (M+H)+

Example 14

3-[2-(2,8-Bis-trifluoromethyl-quinolin-4-yl)-2H-pyrazol-3-yl]-1-pyridin-4-yl-1H-pyridazin-4-one

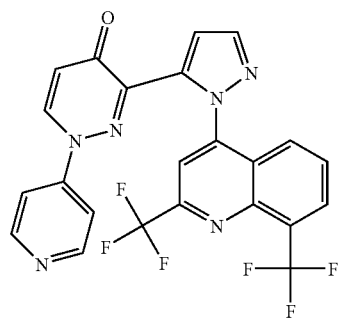 [SMILES: O=c1ccn(-c2ccncc2)nc1-c1ccnn1-c1cc(C(F)(F)F)nc2c(C(F)(F)F)cccc12]

3-[2-(2,8-Bis-trifluoromethyl-quinolin-4-yl)-2H-pyrazol-3-yl]-1-pyridin-4-yl-1H-pyridazin-4-one was obtained in analogy to the method of example 1 from intermediate A-1 and (2,8-bis-trifluoromethyl-quinolin-4-yl)-hydrazine. MS: M=502.8 (M+H)+

Example 15

3-[2-(2,3-Dihydro-benzo[1,4]dioxin-6-yl)-2H-pyrazol-3-yl]-1-pyridin-4-yl-1H-pyridazin-4-one

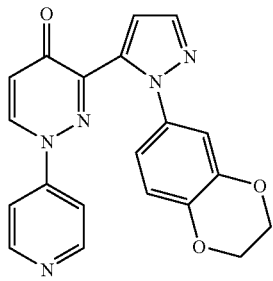 [SMILES: O=c1ccn(-c2ccncc2)nc1-c1ccnn1-c1ccc2c(c1)OCCO2]

3-[2-(2,3-Dihydro-benzo[1,4]dioxin-6-yl)-2H-pyrazol-3-yl]-1-pyridin-4-yl-1H-pyridazin-4-one was obtained in analogy to the method of example 1 from intermediate A-1 and (2,3-dihydro-benzo[1,4]dioxin-6-yl)-hydrazine. MS: M=374.0 (M+H)+

Example 16

1-(2-Methanesulfonyl-pyridin-4-yl)-3-(2-naphthalen-1-yl-2H-1-pyrazol-3-yl)-1H-pyridazin-4-one

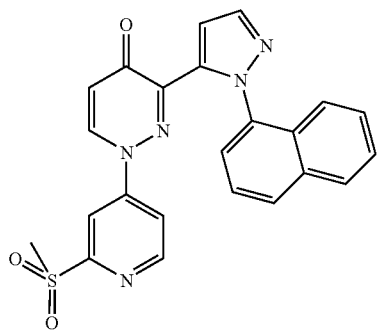 [SMILES: CS(=O)(=O)c1cc(-n2ccc(=O)c(-c3ccnn3-c3cccc4ccccc34)n2)ccn1]

1-(2-Methanesulfonyl-pyridin-4-yl)-3-(2-naphthalen-1-yl-2H-pyrazol-3-yl)-1H-pyridazin-4-one was obtained in analogy to the method of example 1 from intermediate A-3 and naphthalen-1-yl-hydrazine. MS: M=443.9 (M+H)+

Example 17

3-[2-(2,3-Dihydro-benzo[1,4]dioxin-6-yl)-2H-pyrazol-3-yl]-1-(2-methanesulfonyl-pyridin-4-yl)-1H-1-pyridazin-4-one

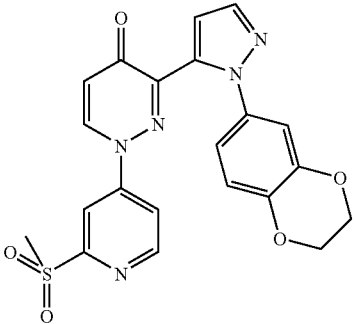 [SMILES: CS(=O)(=O)c1cc(-n2ccc(=O)c(-c3ccnn3-c3ccc4c(c3)OCCO4)n2)ccn1]

3-[2-(2,3-Dihydro-benzo[1,4]dioxin-6-yl)-2H-pyrazol-3-yl]-1-(2-methanesulfonyl-pyridin-4-yl)-1H-pyridazin-4-one was obtained in analogy to the method of example 1 from intermediate A-3 and (2,3-dihydro-benzo[1,4]dioxin-6-yl)-hydrazine.
MS: M=451.8 (M+H)+

Example 18

3-[2-(3-Chloro-phenyl)-2H-pyrazol-3-yl]-1-pyridin-4-yl-1H-pyridazin-4-one

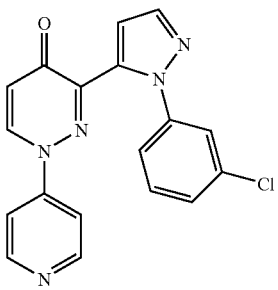 [SMILES: O=c1ccn(-c2ccncc2)nc1-c1ccnn1-c1cccc(Cl)c1]

3-[2-(3-Chloro-phenyl)-2H-pyrazol-3-yl]-1-pyridin-4-yl-1H-pyridazin-4-one was obtained in analogy to the method of example 1 from intermediate A-1 and 3-chloro-phenylhydrazine. MS: M=350.1 (M+H)+

Example 19

3-[2-(2-Methyl-pyridin-4-yl)-2H-pyrazol-3-yl]-1-pyridin-4-yl-1H-pyridazin-4-one

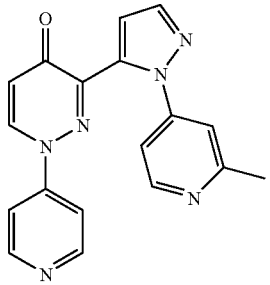 [SMILES: Cc1cc(-n2nccc2-c2nn(-c3ccncc3)ccc2=O)ccn1]

3-[2-(2-Methyl-pyridin-4-yl)-2H-pyrazol-3-yl]-1-pyridin-4-yl-1H-pyridazin-4-one was obtained in analogy to the method of example 1 from intermediate A-1 and (2-methylpyridin-4-yl)-hydrazine. MS: M=331.1 (M+H)+

Example 20

1-Pyridin-4-yl-3-(2-quinolin-4-yl-2H-pyrazol-3-yl)-1H-pyridazin-4-one

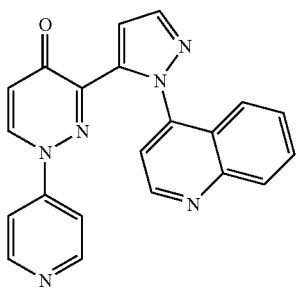 [SMILES: O=c1ccn(-c2ccncc2)nc1-c1ccnn1-c1ccnc2ccccc12]

Pyridin-4-yl-3-(2-quinolin-4-yl-2H-pyrazol-3-yl)-1H-pyridazin-4-one was obtained in analogy to the method of example 1 from intermediate A-1 and quinolin-4-yl-hydrazine. MS: M=367.1 (M+H)$^+$

Example 21

3-(2-Isoquinolin-5-yl-2H-pyrazol-3-yl)-1-pyridin-4-yl-1H-pyridazin-4-one

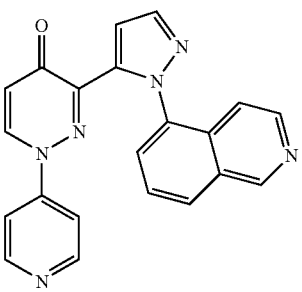 [SMILES: O=c1ccn(-c2ccncc2)nc1-c1ccnn1-c1cccc2cnccc12]

3-(2-Isoquinolin-5-yl-2H-pyrazol-3-yl)-1-pyridin-4-yl-1H-pyridazin-4-one was obtained in analogy to the method of example 1 from intermediate A-1 and isoquinolin-5-yl-hydrazine. MS: M=367.1 (M+H)$^+$

Example 22

1-Pyridin-4-yl-3-(2-quinolin-5-yl-2H-pyrazol-3-yl)-1H-pyridazin-4-one

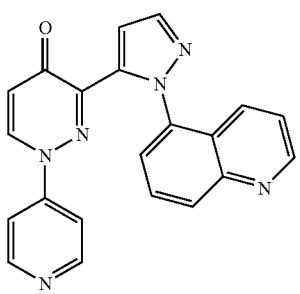 [SMILES: O=c1ccn(-c2ccncc2)nc1-c1ccnn1-c1cccc2ncccc12]

Pyridin-4-yl-3-(2-quinolin-5-yl-2H-pyrazol-3-yl)-1H-pyridazin-4-one was obtained in analogy to the method of example 1 from intermediate A-1 and quinolin-5-yl-hydrazine. MS: M=367.1 (M+H)$^+$

Example 23

3-[2-(2-Chloro-pyridin-4-yl)-2H-pyrazol-3-yl]-1-pyridin-4-yl-1H-pyridazin-4-one

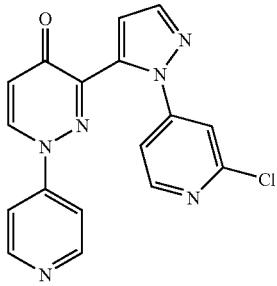 [SMILES: O=c1ccn(-c2ccncc2)nc1-c1ccnn1-c1ccnc(Cl)c1]

3-[2-(2-Chloro-pyridin-4-yl)-2H-pyrazol-3-yl]-1-pyridin-4-yl-1H-pyridazin-4-one was obtained in analogy to the method of example 1 from intermediate A-1 and (2-chloro-pyridin-4-yl)-hydrazine. MS: M=351.1 (M+H)$^+$

Example 24

3-{2-[2-(4-Methyl-piperazin-1-yl)-pyridin-4-yl]-2H-pyrazol-3-yl}-1-pyridin-4-yl-1H-pyridazin-4-one

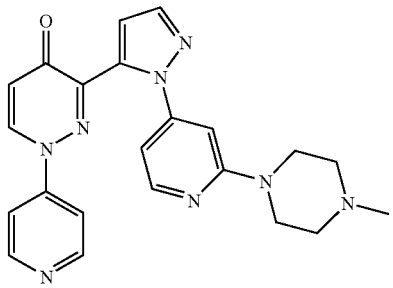 [SMILES: CN1CCN(c2cc(-n3nccc3-c3nn(-c4ccncc4)ccc3=O)ccn2)CC1]

3-{2-[2-(4-Methyl-piperazin-1-yl)-pyridin-4-yl]-2H-pyrazol-3-yl}-1-pyridin-4-yl-1H-pyridazin-4-one was obtained in analogy to the method of example 1 from intermediate A-1 and 2-(4-methyl-piperazin-1-yl)-pyridin-4-yl-hydrazine. MS: M=415.2 (M+H)$^+$

Example 25

3-[2-(2-Piperazin-1-yl-pyridin-4-yl)-2H-pyrazol-3-yl]-1-pyridin-4-yl-1H-pyridazin-4-one

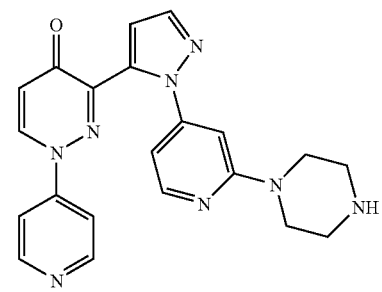 [SMILES: O=c1ccn(-c2ccncc2)nc1-c1ccnn1-c1ccnc(N2CCNCC2)c1]

3-[2-(2-Piperazin-1-yl-pyridin-4-yl)-2H-pyrazol-3-yl]-1-pyridin-4-yl-1H-pyridazin-4-one was obtained in analogy to the method of example 1 from intermediate A-1 and 2-piperazin-1-yl-pyridin-4-yl-hydrazine. MS: M=401.2 (M+H)⁺

Example 26

1-Pyridin-4-yl-3-(2-quinolin-8-yl-2H-pyrazol-3-yl)-1H-pyridazin-4-one

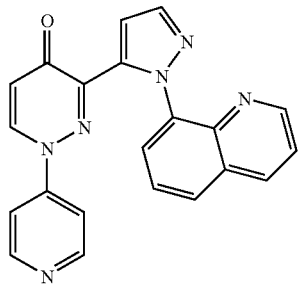 [SMILES: O=c1ccn(-c2ccncc2)nc1-c1ccnn1-c1cccc2cccnc12]

Pyridin-4-yl-3-(2-quinolin-8-yl-2H-pyrazol-3-yl)-1H-pyridazin-4-one was obtained in analogy to the method of example 1 from intermediate A-1 and quinolin-8-yl-hydrazine. MS: M=367.1 (M+H)⁺

Example 27

3-(2-Isoquinolin-8-yl-2H-pyrazol-3-yl)-1-pyridin-4-yl-1H-pyridazin-4-one

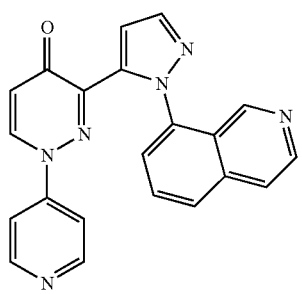 [SMILES: O=c1ccn(-c2ccncc2)nc1-c1ccnn1-c1cccc2ccncc12]

3-(2-Isoquinolin-8-yl-2H-pyrazol-3-yl)-1-pyridin-4-yl-1H-pyridazin-4-one was obtained in analogy to the method of example 1 from intermediate A-1 and isoquinolin-8-yl-hydrazine. MS: M=367.1 (M+H)⁺

Example 28

N,N-Dimethyl-3-[5-(4-oxo-1-pyridin-4-yl-1,4-dihydro-pyridazin-3-yl)-pyrazol-1-yl]-benzenesulfonamide

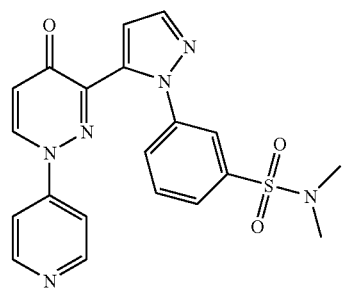 [SMILES: CN(C)S(=O)(=O)c1cccc(-n2nccc2-c2nn(-c3ccncc3)ccc2=O)c1]

N,N-Dimethyl-3-[5-(4-oxo-1-pyridin-4-yl-1,4-dihydro-pyridazin-3-yl)-pyrazol-1-yl]-benzenesulfonamide was obtained in analogy to the method of example 1 from intermediate A-1 and 3-hydrazino-N,N-dimethyl-benzenesulfonamide. MS: M=423.1 (M+H)⁺

Example 29

3-[2-(2,3-Difluoro-phenyl)-2H-pyrazol-3-yl]-1-pyridin-4-yl-1H-pyridazin-4-one

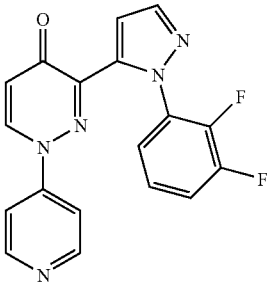 [SMILES: O=c1ccn(-c2ccncc2)nc1-c1ccnn1-c1cccc(F)c1F]

3-[2-(2,3-Difluoro-phenyl)-2H-pyrazol-3-yl]-1-pyridin-4-yl-1H-pyridazin-4-one was obtained in analogy to the method of example 1 from intermediate A-1 and 2,3-difluoro-phenylhydrazine. MS: M=352.1 (M+H)⁺

Example 30

3-(2-Phenyl-2H-pyrazol-3-yl)-1-pyridin-4-yl-1H-pyridazin-4-one

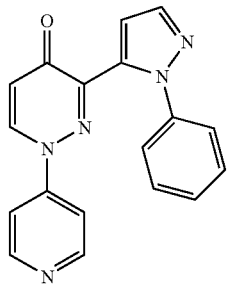 [SMILES: O=c1ccn(-c2ccncc2)nc1-c1ccnn1-c1ccccc1]

3-(2-Phenyl-2H-pyrazol-3-yl)-1-pyridin-4-yl-1H-pyridazin-4-one was obtained in analogy to the method of example 1 from intermediate A-1 and phenylhydrazine. MS: M=316.1 (M+H)⁺

Example 31

1-Pyridin-4-yl-3-(2-pyridin-4-yl-2H-pyrazol-3-yl)-1H-pyridazin-4-one

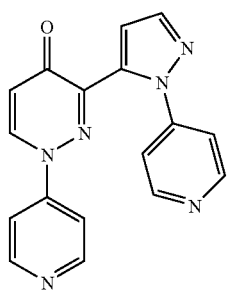 [SMILES: O=c1ccn(-c2ccncc2)nc1-c1ccnn1-c1ccncc1]

Pyridin-4-yl-3-(2-pyridin-4-yl-2H-pyrazol-3-yl)-1H-pyridazin-4-one was obtained in analogy to the method of example 1 from intermediate A-1 and pyridin-4-yl-hydrazine. MS: M=317.1 (M+H)+

Example 32

3-(2-Benzo[1,3]dioxol-5-yl-2H-pyrazol-3-yl)-1-pyridin-3-yl-1H-pyridazin-4-one

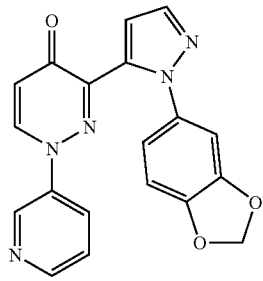 [SMILES: O=c1ccn(-c2cccnc2)nc1-c1ccnn1-c1ccc2c(c1)OCO2]

3-(2-Benzo[1,3]dioxol-5-yl-2H-pyrazol-3-yl)-1-pyridin-3-yl-1H-pyridazin-4-one was obtained in analogy to the method of example 1 from intermediate A-4 and benzo[1,3]dioxol-5-yl-hydrazine. MS: M=360.2 (M+H)+

Example 33

1-Pyridin-3-yl-3-(2-pyridin-2-yl-2H-pyrazol-3-yl)-1H-pyridazin-4-one

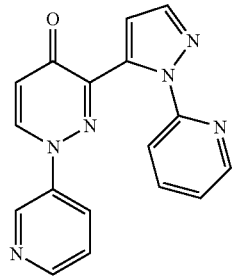 [SMILES: O=c1ccn(-c2cccnc2)nc1-c1ccnn1-c1ccccn1]

Pyridin-3-yl-3-(2-pyridin-2-yl-2H-pyrazol-3-yl)-1H-pyridazin-4-one was obtained in analogy to the method of example 1 from intermediate A-4 and pyridin-2-yl-hydrazine. MS: M=317.2 (M+H)+

Example 34

3-[2-(2,3-Dihydro-benzo[1,4]dioxin-6-yl)-2H-pyrazol-3-yl]-1-pyridin-3-yl-1H-pyridazin-4-one

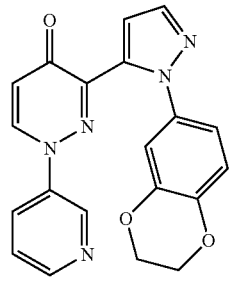 [SMILES: O=c1ccn(-c2cccnc2)nc1-c1ccnn1-c1ccc2c(c1)OCCO2]

3-[2-(2,3-Dihydro-benzo[1,4]dioxin-6-yl)-2H-pyrazol-3-yl]-1-pyridin-3-yl-1H-pyridazin-4-one was obtained in analogy to the method of example 1 from intermediate A-4 and (2,3-dihydro-benzo[1,4]dioxin-6-yl)-hydrazine. MS: M=374.1 (M+H)+

Example 35

3-[2-(3-Fluoro-phenyl)-2H-pyrazol-3-yl]-1-pyridin-3-yl-1H-pyridazin-4-one

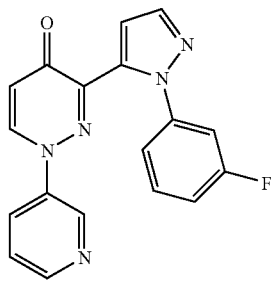 [SMILES: O=c1ccn(-c2cccnc2)nc1-c1ccnn1-c1cccc(F)c1]

3-[2-(3-Fluoro-phenyl)-2H-pyrazol-3-yl]-1-pyridin-3-yl-1H-pyridazin-4-one was obtained in analogy to the method of example 1 from intermediate A-4 and 3-fluoro-phenylhydrazine. MS: M=334.3 (M+H)+

Example 36

3-[2-(2,3-Dihydro-benzo[1,4]dioxin-6-yl)-2H-pyrazol-3-yl]-1-(5-methyl-pyridin-3-yl)-1H-pyridazin-4-one

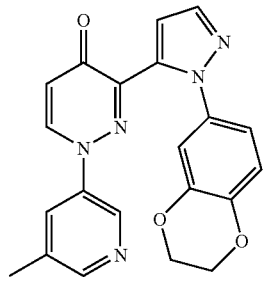 [SMILES: Cc1cncc(-n2ccc(=O)c(-c3ccnn3-c3ccc4c(c3)OCCO4)n2)c1]

3-[2-(2,3-Dihydro-benzo[1,4]dioxin-6-yl)-2H-pyrazol-3-yl]-1-(5-methyl-pyridin-3-yl)-1H-pyridazin-4-one was obtained in analogy to the method of example 1 from intermediate A-5 and (2,3-dihydro-benzo[1,4]dioxin-6-yl)-hydrazine.
MS: M=388.2 (M+H)+

Example 37

3-[2-(3-Fluoro-phenyl)-2H-pyrazol-3-yl]-1-(5-methyl-pyridin-3-yl)-1H-pyridazin-4-one

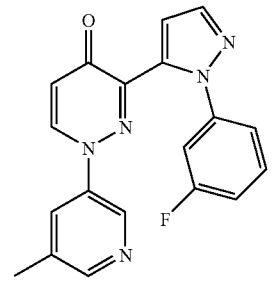 [SMILES: Cc1cncc(-n2ccc(=O)c(-c3ccnn3-c3cccc(F)c3)n2)c1]

3-[2-(3-Fluoro-phenyl)-2H-pyrazol-3-yl]-1-(5-methyl-pyridin-3-yl)-1H-pyridazin-4-one was obtained in analogy to the method of example 1 from intermediate A-5 and 3-fluoro-phenylhydrazine. MS: M=348.2 (M+H)+

Example 38

3-[2-(2,3-Dihydro-benzo[1,4]dioxin-6-yl)-2H-pyrazol-3-yl]-1-(2-methyl-pyridin-4-yl)-1H-pyridazin-4-one

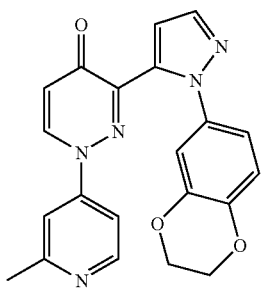 [SMILES: Cc1cc(-n2ccc(=O)c(-c3ccnn3-c3ccc4c(c3)OCCO4)n2)ccn1]

3-[2-(2,3-Dihydro-benzo[1,4]dioxin-6-yl)-2H-pyrazol-3-yl]-1-(2-methyl-pyridin-4yl)-1H-pyridazin-4-one was obtained in analogy to the method of example 1 from intermediate A-6 and (2,3-dihydro-benzo[1,4]dioxin-6-yl)-hydrazine. MS: M=388.1 (M+H)+

Example 39

3-[2-(3-Fluoro-phenyl)-2H-pyrazol-3-yl]-1-(2-methyl-pyridin-4-yl)-1H-pyridazin-4-one

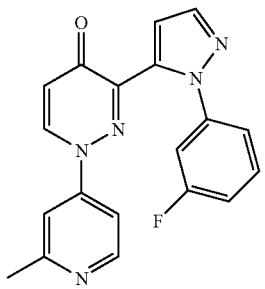 [SMILES: Cc1cc(-n2ccc(=O)c(-c3ccnn3-c3cccc(F)c3)n2)ccn1]

3-[2-(3-Fluoro-phenyl)-2H-pyrazol-3-yl]-1-(2-methyl-pyridin-4-yl)-1H-pyridazin-4-one was obtained in analogy to the method of example 1 from intermediate A-6 and 3-fluoro-phenylhydrazine. MS: M=348.2 (M+H)+

Example 40

3-[2-(3-Fluoro-phenyl)-2H-pyrazol-3-yl]-1-(2-methoxy-pyridin-4-yl)-1H-pyridazin-4-one

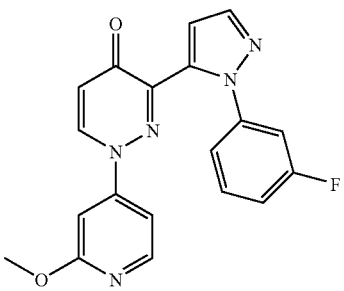 [SMILES: COc1cc(-n2ccc(=O)c(-c3ccnn3-c3cccc(F)c3)n2)ccn1]

3-[2-(3-Fluoro-phenyl)-2H-pyrazol-3-yl]-1-(2-methoxy-pyridin-4-yl)-1H-pyridazin-4-one was obtained in analogy to the method of example 1 from intermediate A-7 and 3-fluoro-phenylhydrazine. MS: M=364.0 (M+H)+

Example 41

3-[2-(2,3-Dihydro-benzo[1,4]dioxin-6-yl)-2H-pyrazol-3-yl]-1-(2-morpholin-4-yl-pyridin-4-yl)-1H-pyridazin-4-one

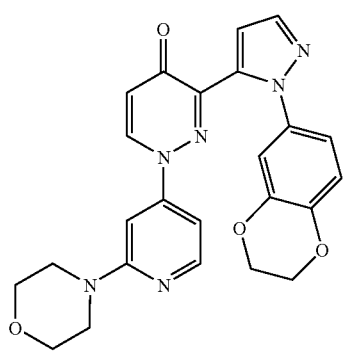 [SMILES: O=c1ccn(-c2ccnc(N3CCOCC3)c2)nc1-c1ccnn1-c1ccc2c(c1)OCCO2]

3-[2-(2,3-Dihydro-benzo[1,4]dioxin-6-yl)-2H-pyrazol-3-yl]-1-(2-morpholin-4-yl-pyridin-4-yl)-1H-pyridazin-4-one was obtained in analogy to the method of example 1 from intermediate A-8 and (2,3-dihydro-benzo[1,4]dioxin-6-yl)-hydrazine. MS: M=459.3 (M+H)+

Example 42

3-[2-(3-Fluoro-phenyl)-2H-pyrazol-3-yl]-1-(2-morpholin-4-yl-pyridin-4-yl)-1H-pyridazin-4-one

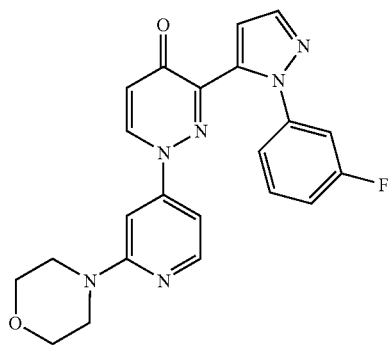 [SMILES: O=c1ccn(-c2ccnc(N3CCOCC3)c2)nc1-c1ccnn1-c1cccc(F)c1]

3-[2-(3-Fluoro-phenyl)-2H-pyrazol-3-yl]-1-(2-morpholin-4-yl-pyridin-4-yl)-1H-pyridazin-4-one was obtained in analogy to the method of example 1 from intermediate A-8 and 3-fluoro-phenylhydrazine. MS: M=419.1 (M+H)+

Example 43

4-{3-[2-(2,3-Dihydro-benzo[1,4]dioxin-6-yl)-2H-pyrazol-3-yl]-4-oxo-4H-pyridazin-1-yl}-pyridine-2-carbonitrile

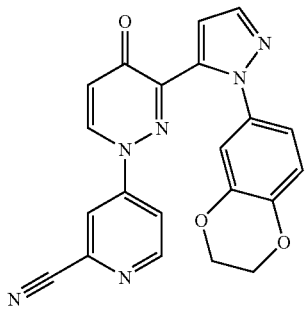 [SMILES: N#Cc1cc(-n2ccc(=O)c(-c3ccnn3-c3ccc4c(c3)OCCO4)n2)ccn1]

4-{3-[2-(2,3-Dihydro-benzo[1,4]dioxin-6-yl)-2H-pyrazol-3-yl]-4-oxo-4H-pyridazin-1-yl}-pyridine-2-carbonitrile was obtained in analogy to the method of example 1 from intermediate A-9 and (2,3-dihydro-benzo[1,4]dioxin-6-yl)-hydrazine. MS: M=399.2 (M+H)$^+$

Example 44

4-{3-[2-(3-Fluoro-phenyl)-2H-pyrazol-3-yl]-4-oxo-4H-pyridazin-1-yl}-pyridine-2-carbonitrile

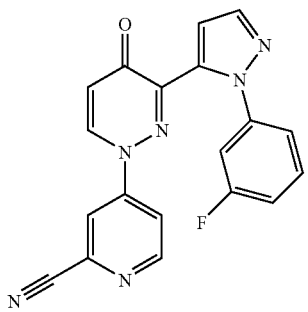 [SMILES: N#Cc1cc(-n2ccc(=O)c(-c3ccnn3-c3cccc(F)c3)n2)ccn1]

4-{3-[2-(3-Fluoro-phenyl)-2H-pyrazol-3-yl]-4-oxo-4H-pyridazin-1-yl}-pyridine-2-carbonitrile was obtained in analogy to the method of example 1 from intermediate A-9 and 3-fluoro-phenylhydrazine. MS: M=359.0 (M+H)$^+$

Example 45

3-[2-(3-Fluoro-phenyl)-2H-pyrazol-3-yl]-1-(5-methanesulfonyl-pyridin-3-yl)-1H-pyridazin-4-one

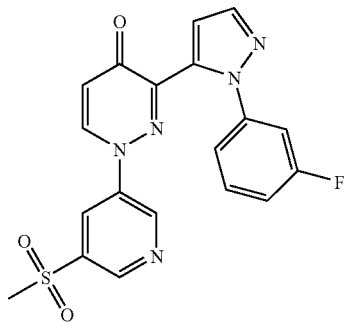 [SMILES: CS(=O)(=O)c1cncc(-n2ccc(=O)c(-c3ccnn3-c3cccc(F)c3)n2)c1]

3-[2-(3-Fluoro-phenyl)-2H-pyrazol-3-yl]-1-(5-methanesulfonyl-pyridin-3-yl)-1H-pyridazin-4-one was obtained in analogy to the method of example 1 from intermediate A-10 and 3-fluoro-phenylhydrazine. MS: M=412.3 (M+H)$^+$

Example 46

3-[2-(2,3-Dihydro-benzo[1,4]dioxin-6-yl)-2H-pyrazol-3-yl]-1-(2-hydroxy-pyridin-4-yl)-1H-pyridazin-4-one

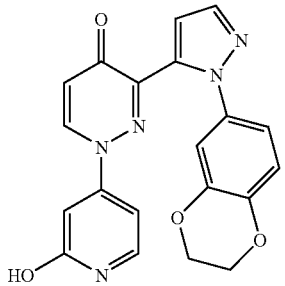 [SMILES: O=c1ccn(-c2ccnc(O)c2)nc1-c1ccnn1-c1ccc2c(c1)OCCO2]

3-[2-(2,3-Dihydro-benzo[1,4]dioxin-6-yl)-2H-pyrazol-3-yl]-1-(2-hydroxy-pyridin-4-yl)-1H-pyridazin-4-one was obtained in analogy to the method of example 1 from intermediate A-7 and (2,3-dihydro-benzo[1,4]dioxin-6-yl)-hydrazine. MS: M=390.0 (M+H)$^+$

Example 47

3-[2-(2,5-Difluoro-phenyl)-2H-pyrazol-3-yl]-1-pyridin-3-yl-1H-pyridazin-4-one

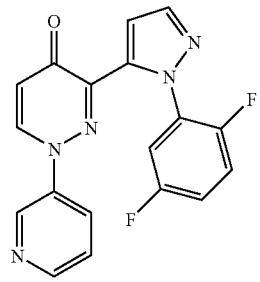 [SMILES: O=c1ccn(-c2cccnc2)nc1-c1ccnn1-c1cc(F)ccc1F]

3-[2-(2,5-Difluoro-phenyl)-2H-pyrazol-3-yl]-1-pyridin-3-yl-1H-pyridazin-4-one was obtained in analogy to the method of example 1 from intermediate A-4 and 2,5-difluoro-phenylhydrazine. MS: M=352.3 (M+H)$^+$

Example 48

3-[2-(6-Fluoro-quinolin-4-yl)-2H-pyrazol-3-yl]-1-(5-methyl-pyridin-3-yl)-1H-pyridazin-4-one

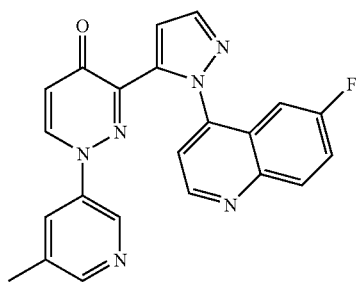 [SMILES: Cc1cncc(-n2ccc(=O)c(-c3ccnn3-c3ccnc4ccc(F)cc34)n2)c1]

3-[2-(6-Fluoro-quinolin-4-yl)-2H-pyrazol-3-yl]-1-(5-methyl-pyridin-3-yl)-1H-pyridazin-4-one was obtained in analogy to the method of example 1 from intermediate A-5 and 6-fluoro-quinolin-4-yl-hydrazine. MS: M=399.1 (M+H)⁻

Example 49

1-(5-Fluoro-pyridin-3-yl)-3-[2-(6-fluoro-quinolin-4-yl)-2H-pyrazol-3-yl]-1H-pyridazin-4-one

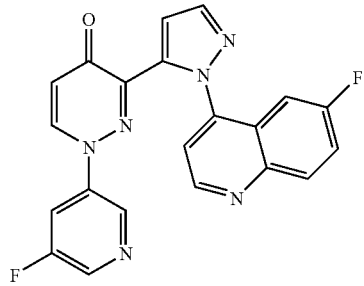 [SMILES: O=c1ccn(-c2cncc(F)c2)nc1-c1ccnn1-c1ccnc2ccc(F)cc12]

1-(5-Fluoro-pyridin-3-yl)-3-[2-(6-fluoro-quinolin-4-yl)-2H-pyrazol-3-yl]-1H-pyridazin-4-one was obtained in analogy to the method of example 1 from intermediate A-11 and 6-fluoro-quinolin-4-yl-hydrazine. MS: M=403.2 (M+H)⁻

Example 50

3-[2-(6-Fluoro-quinolin-4-yl)-2H-pyrazol-3-yl]-1-pyridin-3-yl-1H-pyridazin-4-one

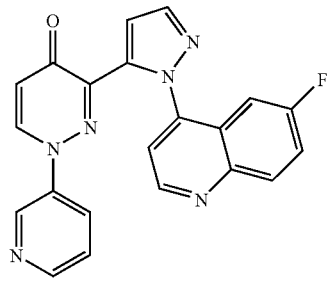 [SMILES: O=c1ccn(-c2cccnc2)nc1-c1ccnn1-c1ccnc2ccc(F)cc12]

3-[2-(6-Fluoro-quinolin-4-yl)-2H-pyrazol-3-yl]-1-pyridin-3-yl-1H-pyridazin-4-one was obtained in analogy to the method of example 1 from intermediate A-4 and 6-fluoro-quinolin-4-yl-hydrazine. MS: M=385.1 (M+H)⁺

Example 51

1-(5-Chloro-pyridin-3-yl)-3-(2-quinolin-4-yl-2H-pyrazol-3-yl)-1H-pyridazin-4-one

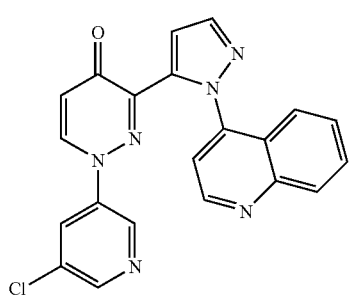 [SMILES: O=c1ccn(-c2cncc(Cl)c2)nc1-c1ccnn1-c1ccnc2ccccc12]

1-(5-Chloro-pyridin-3-yl)-3-(2-quinolin-4-yl-2H-pyrazol-3-yl)-1H-pyridazin-4-one was obtained in analogy to the method of example 1 from intermediate A-12 and quinolin-4-yl-hydrazine. MS: M=401.1 (M+H)⁺

Example 52

1-(5-Chloro-pyridin-3-yl)-3-[2-(6-fluoro-quinolin-4-yl)-2H-pyrazol-3-yl]-1H-pyridazin-4-one

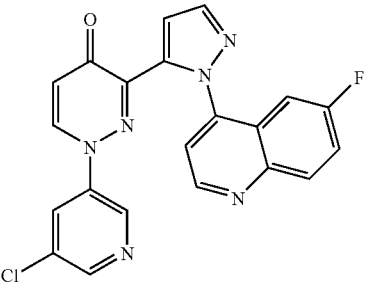 [SMILES: O=c1ccn(-c2cncc(Cl)c2)nc1-c1ccnn1-c1ccnc2ccc(F)cc12]

1-(5-Chloro-pyridin-3-yl)-3-[2-(6-fluoro-quinolin-4-yl)-2H-pyrazol-3-yl]-1H-pyridazin-4-one was obtained in analogy to the method of example 1 from intermediate A-12 and 6-fluoro-quinolin-4-yl-hydrazine. MS: M=419.2 (M+H)⁻

Example 53

3-[2-(3-Chloro-phenyl)-2H-pyrazol-3-yl]-1-(5-chloro-pyridin-3-yl)-1H-pyridazin-4-one

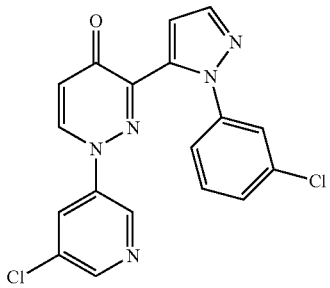 [SMILES: O=c1ccn(-c2cncc(Cl)c2)nc1-c1ccnn1-c1cccc(Cl)c1]

3-[2-(3-Chloro-phenyl)-2H-pyrazol-3-yl]-1-(5-chloro-pyridin-3-yl)-1H-pyridazin-4-one was obtained in analogy to the method of example 1 from intermediate A-12 and 3-chloro-phenylhydrazine. MS: M=384.1 (M+H)⁺

Example 54

1-(2-Chloro-pyridin-4-yl)-3-(2-quinolin-4-yl-2H-pyrazol-3-yl)-1H-pyridazin-4-one

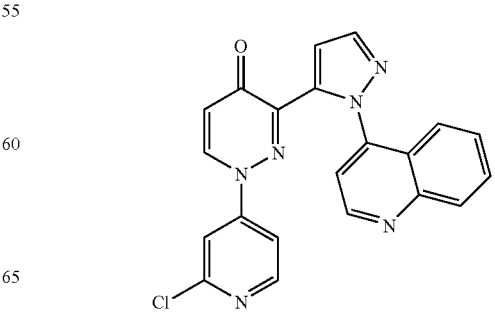

1-(2-Chloro-pyridin-4-yl)-3-(2-quinolin-4-yl-2H-pyrazol-3-yl)-1H-pyridazin-4-one was obtained in analogy to the method of example 1 from intermediate A-2 and quinolin-4-yl-hydrazine. MS: M=401.1 (M+H)⁺

Example 55

1-(2-Chloro-pyridin-4-yl)-3-[2-(6-fluoro-quinolin-4-yl)-2H-pyrazol-3-yl]-1H-pyridazin-4-one

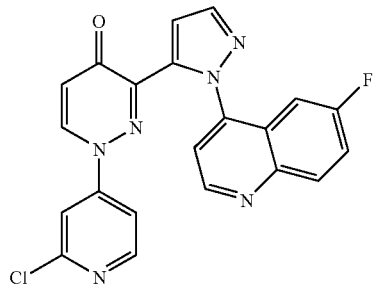 [SMILES: O=c1ccn(-c2ccnc(Cl)c2)nc1-c1ccnn1-c1ccnc2ccc(F)cc12]

1-(2-Chloro-pyridin-4-yl)-3-[2-(6-fluoro-quinolin-4-yl)-2H-pyrazol-3-yl]-1H-pyridazin-4-one was obtained in analogy to the method of example 1 from intermediate A-2 and 6-fluoro-quinolin-4-yl-hydrazine. MS: M=419.2 (M+H)⁻

Example 56

3-[2-(3-Chloro-phenyl)-2H-pyrazol-3-yl]-1-(2-chloro-pyridin-4-yl)-1H-pyridazin-4-one

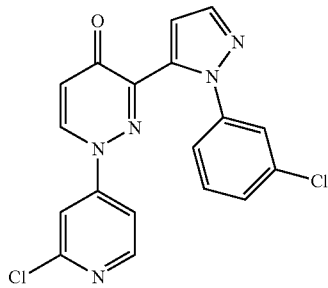 [SMILES: O=c1ccn(-c2ccnc(Cl)c2)nc1-c1ccnn1-c1cccc(Cl)c1]

3-[2-(3-Chloro-phenyl)-2H-pyrazol-3-yl]-1-(2-chloro-pyridin-4-yl)-1H-pyridazin-4-one was obtained in analogy to the method of example 1 from intermediate A-2 and 3-chlorophenylhydrazine. MS: M=384.8 (M+H)⁺

Example 57

1-(2-Chloro-pyridin-4-yl)-3-[2-(2-chloro-pyridin-4-yl)-2H-pyrazol-3-yl]-1H-pyridazin-4-one

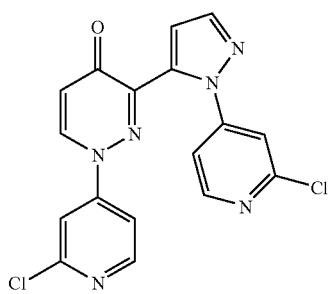 [SMILES: O=c1ccn(-c2ccnc(Cl)c2)nc1-c1ccnn1-c1ccnc(Cl)c1]

1-(2-Chloro-pyridin-4-yl)-3-[2-(2-chloro-pyridin-4-yl)-2H-pyrazol-3-yl]-1H-pyridazin-4-one was obtained in analogy to the method of example 1 from intermediate A-2 and 2-chloro-pyridin-4-yl-hydrazine. MS: M=385.0 (M+H)⁺

Example 58

1-(2-Chloro-pyridin-4-yl)-3-(2-quinolin-5-yl-2H-pyrazol-3-yl)-1H-pyridazin-4-one

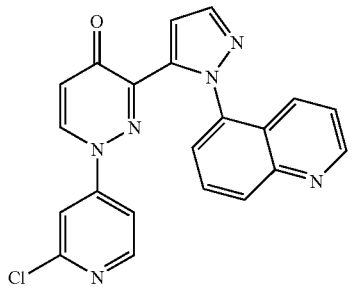 [SMILES: O=c1ccn(-c2ccnc(Cl)c2)nc1-c1ccnn1-c1cccc2ncccc12]

1-(2-Chloro-pyridin-4-yl)-3-(2-quinolin-5-yl-2H-pyrazol-3-yl)-1H-pyridazin-4-one was obtained in analogy to the method of example 1 from intermediate A-2 and quinolin-5-yl-hydrazine. MS: M=401.1 (M+H)⁺

Example 59

1-(2-Chloro-pyridin-4-yl)-3-(2-isoquinolin-5-yl-2H-pyrazol-3-yl)-1H-pyridazin-4-one

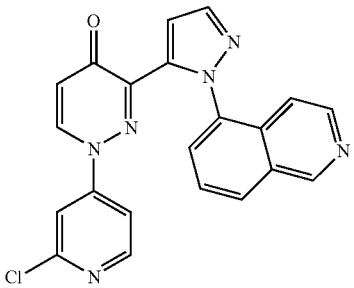 [SMILES: O=c1ccn(-c2ccnc(Cl)c2)nc1-c1ccnn1-c1cccc2cnccc12]

1-(2-Chloro-pyridin-4-yl)-3-(2-isoquinolin-5-yl-2H-pyrazol-3-yl)-1H-pyridazin-4-one was obtained in analogy to the method of example 1 from intermediate A-2 and isoquinolin-5-yl-hydrazine. MS: M=401.1 (M+H)⁺

Example 60

1-(5-Chloro-pyridin-3-yl)-3-(2-quinolin-5-yl-2H-pyrazol-3-yl)-1H-pyridazin-4-one

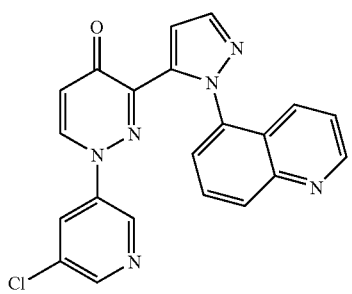 [SMILES: O=c1ccn(-c2cncc(Cl)c2)nc1-c1ccnn1-c1cccc2ncccc12]

1-(5-Chloro-pyridin-3-yl)-3-(2-quinolin-5-yl-2H-pyrazol-3-yl)-1H-pyridazin-4-one was obtained in analogy to the method of example 1 from intermediate A-12 and quinolin-5-yl-hydrazine. MS: M=401.1 (M+H)+

Example 61

1-(5-Chloro-pyridin-3-yl)-3-[2-(6-chloro-quinolin-4-yl)-2H-pyrazol-3-yl]-1H-pyridazin-4-one

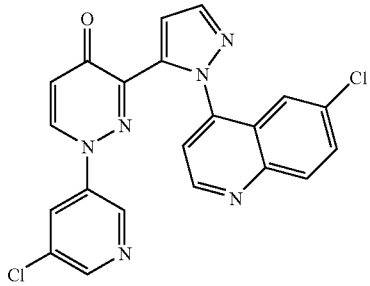 [SMILES: O=c1ccn(-c2cncc(Cl)c2)nc1-c1ccnn1-c1ccnc2ccc(Cl)cc12]

1-(5-Chloro-pyridin-3-yl)-3-[2-(6-chloro-quinolin-4-yl)-2H-pyrazol-3-yl]-1H-pyridazin-4-one was obtained in analogy to the method of example 1 from intermediate A-12 and 6-chloro-quinolin-4-yl-hydrazine. MS: M=435.2 (M+H)−

Example 62

1-(2-Chloro-pyridin-4-yl)-3-[2-(6-chloro-quinolin-4-yl)-2H-pyrazol-3-yl]-1H-pyridazin-4-one

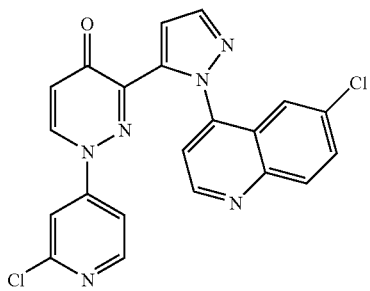 [SMILES: O=c1ccn(-c2ccnc(Cl)c2)nc1-c1ccnn1-c1ccnc2ccc(Cl)cc12]

1-(2-Chloro-pyridin-4-yl)-3-[2-(6-chloro-quinolin-4-yl)-2H-pyrazol-3-yl]-1H-pyridazin-4-one was obtained in analogy to the method of example 1 from intermediate A-2 and 6-chloro-quinolin-4-yl-hydrazine. MS: M=435.2 (M+H)−

Example 63

1-(2-Chloro-pyridin-4-yl)-3-[2-(2-fluoro-phenyl)-2H-pyrazol-3-yl]-1H-pyridazin-4-one

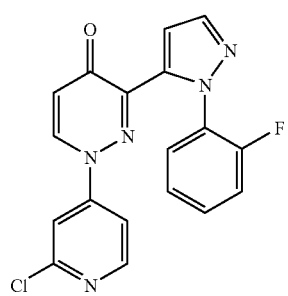 [SMILES: O=c1ccn(-c2ccnc(Cl)c2)nc1-c1ccnn1-c1ccccc1F]

1-(2-Chloro-pyridin-4-yl)-3-[2-(2-fluoro-phenyl)-2H-pyrazol-3-yl]-1H-pyridazin-4-one was obtained in analogy to the method of example 1 from intermediate A-2 and 2-fluoro-phenylhydrazine. MS: M=368.0 (M+H)+

Example 64

1-(5-Chloro-pyridin-3-yl)-3-[2-(2-fluoro-phenyl)-2H-pyrazol-3-yl]-1H-pyridazin-4-one

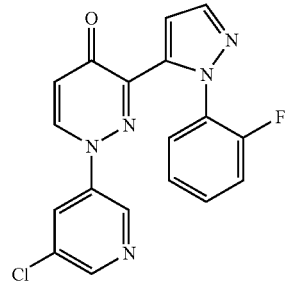 [SMILES: O=c1ccn(-c2cncc(Cl)c2)nc1-c1ccnn1-c1ccccc1F]

1-(5-Chloro-pyridin-3-yl)-3-[2-(2-fluoro-phenyl)-2H-pyrazol-3-yl]-1H-pyridazin-4-one was obtained in analogy to the method of example 1 from intermediate A-12 and 2-fluoro-phenylhydrazine. MS: M=368.0 (M+H)+

Example 65

3-[2-(2-Fluoro-phenyl)-2H-pyrazol-3-yl]-1-isoquinolin-4-yl-1H-pyridazin-4-one

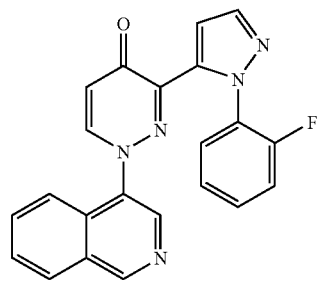 [SMILES: O=c1ccn(-c2cncc3ccccc23)nc1-c1ccnn1-c1ccccc1F]

3-[2-(2-Fluoro-phenyl)-2H-pyrazol-3-yl]-1-isoquinolin-4-yl-1H-pyridazin-4-one was obtained in analogy to the method of example 1 from intermediate A-13 and 2-fluoro-phenylhydrazine. MS: M=384.1 (M+H)+

Example 66

3-[2-(3-Chloro-phenyl)-2H-pyrazol-3-yl]-1-isoquinolin-4-yl-1H-pyridazin-4-one

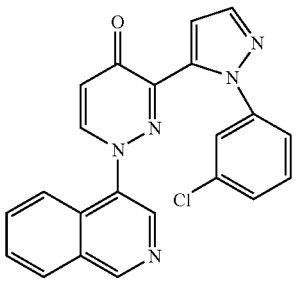 [SMILES: O=c1ccn(-c2cncc3ccccc23)nc1-c1ccnn1-c1cccc(Cl)c1]

3-[2-(3-Chloro-phenyl)-2H-pyrazol-3-yl]-1-isoquinolin-4-yl-1H-pyridazin-4-one was obtained in analogy to the method of example 1 from intermediate A-13 and 3-chloro-phenylhydrazine. MS: M=400.2 (M+H)+

Example 67

3-[2-(3-Chloro-phenyl)-2H-pyrazol-3-yl]-1-(5-trifluoromethyl-pyridin-3-yl)-1H-pyridazin-4-one

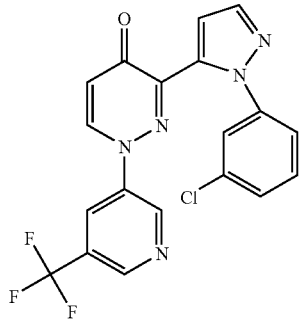 [SMILES: O=c1ccn(-c2cncc(C(F)(F)F)c2)nc1-c1ccnn1-c1cccc(Cl)c1]

3-[2-(3-Chloro-phenyl)-2H-pyrazol-3-yl]-1-(5-trifluoromethyl-pyridin-3-yl)-1H-pyridazin-4-one was obtained in analogy to the method of example 1 from intermediate A-14 and 3-chloro-phenylhydrazine. MS: M=418.1 (M+H)+

Example 68

3-[2-(2-Fluoro-phenyl)-2H-pyrazol-3-yl]-1-(5-trifluoromethyl-pyridin-3-yl)-1H-pyridazin-4-one

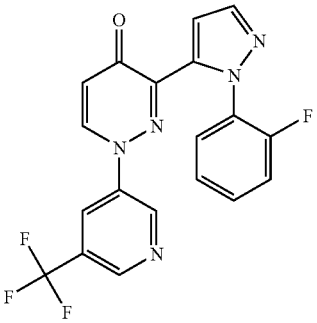 [SMILES: O=c1ccn(-c2cncc(C(F)(F)F)c2)nc1-c1ccnn1-c1ccccc1F]

3-[2-(2-Fluoro-phenyl)-2H-pyrazol-3-yl]-1-(5-trifluoromethyl-pyridin-3-yl)-1H-pyridazin-4-one was obtained in analogy to the method of example 1 from intermediate A-14 and 2-fluoro-phenylhydrazine. MS: M=402.2 (M+H)+

Example 69

1-(2-Chloro-pyridin-4-yl)-3-[2-(7-chloro-quinolin-4-yl)-2H-pyrazol-3-yl]-1H-pyridazin-4-one

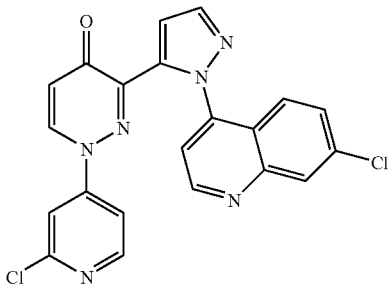 [SMILES: O=c1ccn(-c2ccnc(Cl)c2)nc1-c1ccnn1-c1ccnc2cc(Cl)ccc12]

1-(2-Chloro-pyridin-4-yl)-3-[2-(7-chloro-quinolin-4-yl)-2H-pyrazol-3-yl]-1H-pyridazin-4-one was obtained in analogy to the method of example 1 from intermediate A-2 and 7-chloro-quinolin-4-yl-hydrazine. MS: M=435.2 (M+H)+

Example 70

1-(5-Chloro-pyridin-3-yl)-3-[2-(7-chloro-quinolin-4-yl)-2H-pyrazol-3-yl]-1H-pyridazin-4-one

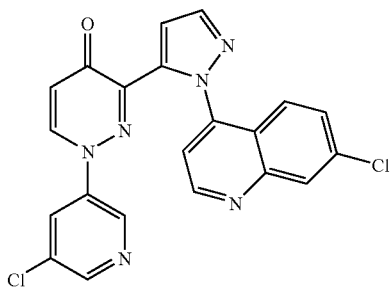 [SMILES: O=c1ccn(-c2cncc(Cl)c2)nc1-c1ccnn1-c1ccnc2cc(Cl)ccc12]

1-(5-Chloro-pyridin-3-yl)-3-[2-(7-chloro-quinolin-4-yl)-2H-pyrazol-3-yl]-1H-pyridazin-4-one was obtained in analogy to the method of example 1 from intermediate A-12 and 7-chloro-quinolin-4-yl-hydrazine. MS: M=435.2 (M+H)+

Example 71

3-(2-Quinolin-4-yl-2H-pyrazol-3-yl)-1-(5-trifluoromethyl-pyridin-3-yl)-1H-pyridazin-4-one

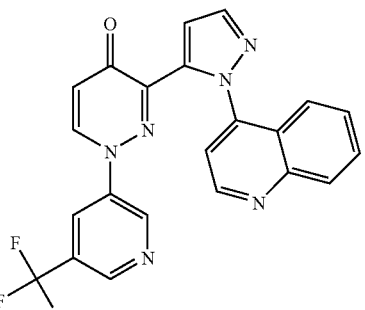

3-(2-Quinolin-4-yl-2H-pyrazol-3-yl)-1-(5-trifluoromethyl-pyridin-3-yl)-1H-pyridazin-4-one was obtained in analogy to the method of example 1 from intermediate A-14 and quinolin-4-yl-hydrazine. MS: M=435.3 (M+H)+

Example 72

3-[2-(6-Chloro-quinolin-4-yl)-2H-pyrazol-3-yl]-1-pyridin-4-yl-1H-pyridazin-4-one

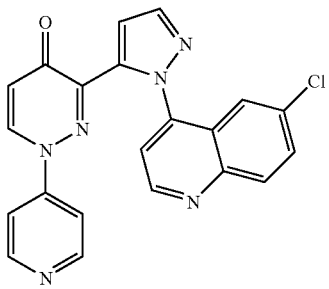 [SMILES: O=c1ccn(-c2ccncc2)nc1-c1ccnn1-c1ccnc2ccc(Cl)cc12]

3-[2-(6-Chloro-quinolin-4-yl)-2H-pyrazol-3-yl]-1-pyridin-4-yl-1H-pyridazin-4-one was obtained in analogy to the method of example 1 from intermediate A-1 and 6-chloro-quinolin-4-yl-hydrazine. MS: M=401.1 (M+H)+

Example 73

3-(2-Isoquinolin-4-yl-2H-pyrazol-3-yl)-1-pyridin-4-yl-1H-pyridazin-4-one

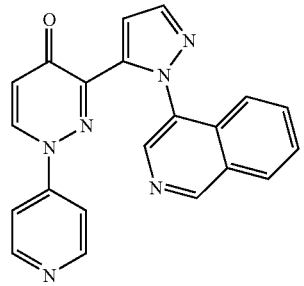 [SMILES: O=c1ccn(-c2ccncc2)nc1-c1ccnn1-c1cncc2ccccc12]

3-(2-Isoquinolin-4-yl-2H-pyrazol-3-yl)-1-pyridin-4-yl-1H-pyridazin-4-one was obtained in analogy to the method of example 1 from intermediate A-1 and isoquinolin-4-yl-hydrazine. MS: M=367.0 (M+H)+

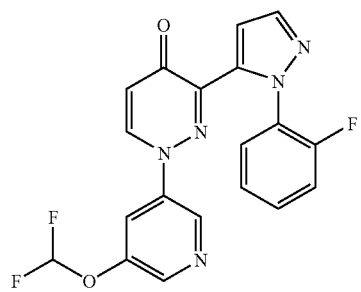 [SMILES: O=c1ccn(-c2cncc(OC(F)F)c2)nc1-c1ccnn1-c1ccccc1F]

1-(5-Difluoromethoxy-pyridin-3-yl)-3-[2-(2-fluoro-phenyl)-2H-pyrazol-3-yl]-1H-pyridazin-4-one was obtained in analogy to the method of example 1 from intermediate A-15 and 2-fluoro-phenylhydrazine. MS: M=400.1 (M+H)+

Example 75

3-[2-(2-Fluoro-phenyl)-2H-pyrazol-3-yl]-1-(6-trifluoromethyl-pyridin-3-yl)-1H-pyridazin-4-one

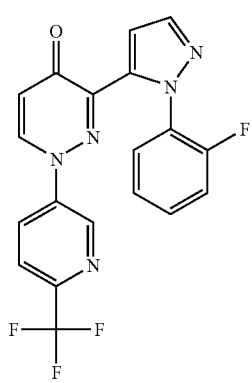 [SMILES: O=c1ccn(-c2ccc(C(F)(F)F)nc2)nc1-c1ccnn1-c1ccccc1F]

3-[2-(2-Fluoro-phenyl)-2H-pyrazol-3-yl]-1-(6-trifluoromethyl-pyridin-3-yl)-1H-pyridazin-4-one was obtained in analogy to the method of example 1 from intermediate A-16 and 2-fluoro-phenylhydrazine. MS: M=402.2 (M+H)+

Example 76

5-{3-[2-(2-Fluoro-phenyl)-2H-pyrazol-3-yl]-4-oxo-4H-pyridazin-1-yl}-pyridine-2-carbonitrile

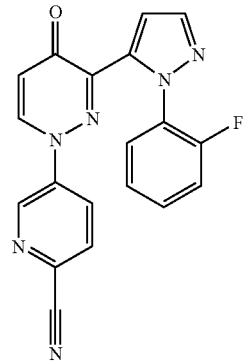 [SMILES: N#Cc1ccc(-n2ccc(=O)c(-c3ccnn3-c3ccccc3F)n2)cn1]

5-{3-[2-(2-Fluoro-phenyl)-2H-pyrazol-3-yl]-4-oxo-4H-pyridazin-1-yl}-pyridine-2-carbonitrile was obtained in analogy to the method of example 1 from intermediate A-17 and 2-fluoro-phenylhydrazine. MS: M=359.1 (M+H)+

Example 77

1-(6-Chloro-pyridin-3-yl)-3-[2-(2-fluoro-phenyl)-2H-pyrazol-3-yl]-1H-pyridazin-4-one

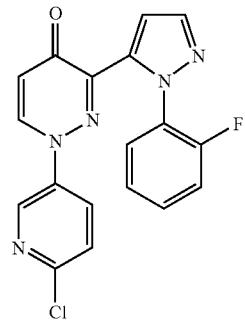 [SMILES: O=c1ccn(-c2ccc(Cl)nc2)nc1-c1ccnn1-c1ccccc1F]

1-(6-Chloro-pyridin-3-yl)-3-[2-(2-fluoro-phenyl)-2H-pyrazol-3-yl]-1H-pyridazin-4-one was obtained in analogy to the method of example 1 from intermediate A-18 and 2-fluoro-phenylhydrazine. MS: M=368.0 (M+H)+

Example 78

3-[2-(2-Fluoro-phenyl)-2H-pyrazol-3-yl]-1-quinolin-3-yl-1H-pyridazin-4-one

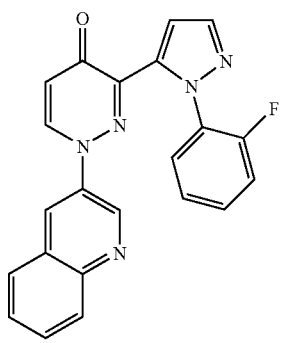 [SMILES: O=c1ccn(-c2cnc3ccccc3c2)nc1-c1ccnn1-c1ccccc1F]

3-[2-(2-Fluoro-phenyl)-2H-pyrazol-3-yl]-1-quinolin-3-yl-1H-pyridazin-4-one was obtained in analogy to the method of example 1 from intermediate A-19 and 2-fluorophenylhydrazine. MS: M=384.1 (M+H)+

Example 79

1-(2-Methyl-pyridin-4-yl)-3-(2-quinolin-4-yl-2H-pyrazol-3-yl)-1H-pyridazin-4-one

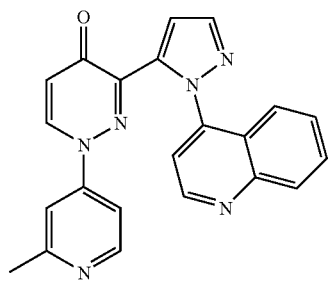 [SMILES: Cc1cc(-n2ccc(=O)c(-c3ccnn3-c3ccnc4ccccc34)n2)ccn1]

1-(2-Methyl-pyridin-4-yl)-3-(2-quinolin-4-yl-2H-pyrazol-3-yl)-1H-pyridazin-4-one was obtained in analogy to the method of example 1 from intermediate A-6 and quinolin-4-yl-hydrazine. MS: M=381.3 (M+H)+

Example 80

3-(2-Quinolin-5-yl-2H-pyrazol-3-yl)-1-(6-trifluoromethyl-pyridin-3-yl)-1H-pyridazin-4-one

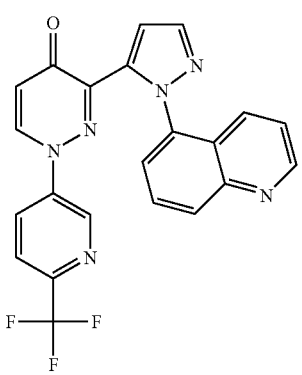 [SMILES: O=c1ccn(-c2ccc(C(F)(F)F)nc2)nc1-c1ccnn1-c1cccc2ncccc12]

3-(2-Quinolin-5-yl-2H-pyrazol-3-yl)-1-(6-trifluoromethyl-pyridin-3-yl)-1H-pyridazin-4-one was obtained in analogy to the method of example 1 from intermediate A-16 and quinolin-5-yl-hydrazine. MS: M=435.3 (M+H)+

Example 81

3-(2-Isoquinolin-5-yl-2H-pyrazol-3-yl)-1-(6-trifluoromethyl-pyridin-3-yl)-1H-pyridazin-4-one

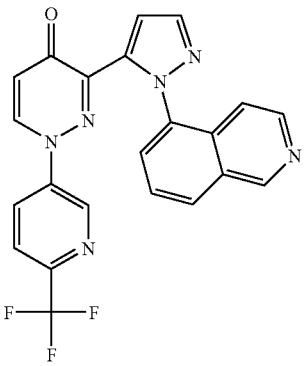 [SMILES: O=c1ccn(-c2ccc(C(F)(F)F)nc2)nc1-c1ccnn1-c1cccc2cnccc12]

3-(2-Isoquinolin-5-yl-2H-pyrazol-3-yl)-1-(6-trifluoromethyl-pyridin-3-yl)-1H-pyridazin-4-one was obtained in analogy to the method of example 1 from intermediate A-16 and isoquinolin-5-yl-hydrazine. MS: M=435.3 (M+H)+

Example 82

3-[2-(7-Chloro-quinolin-4-yl)-2H-pyrazol-3-yl]-1-(5-methyl-pyridin-3-yl)-1H-pyridazin-4-one

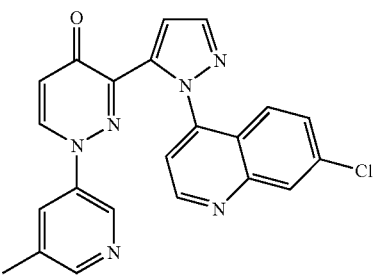 [SMILES: Cc1cncc(-n2ccc(=O)c(-c3ccnn3-c3ccnc4cc(Cl)ccc34)n2)c1]

3-[2-(7-Chloro-quinolin-4-yl)-2H-pyrazol-3-yl]-1-(5-methyl-pyridin-3-yl)-1H-pyridazin-4-one was obtained in analogy to the method of example 1 from intermediate A-5 and 7-chloro-quinolin-4-yl-hydrazine. MS: M=415.2 (M+H)+

Example 83

1-(2-Methyl-pyridin-4-yl)-3-(2-quinolin-5-yl-2H-pyrazol-3-yl)-1H-pyridazin-4-one

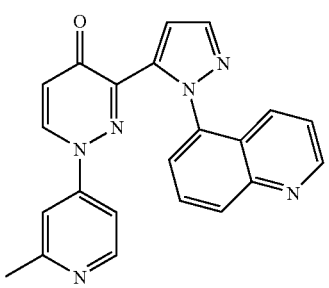 [SMILES: Cc1cc(-n2ccc(=O)c(-c3ccnn3-c3cccc4ncccc34)n2)ccn1]

1-(2-Methyl-pyridin-4-yl)-3-(2-quinolin-5-yl-2H-pyrazol-3-yl)-1H-pyridazin-4-one was obtained in analogy to the method of example 1 from intermediate A-6 and quinolin-5-yl-hydrazine. MS: M=381.3 (M+H)⁺

Example 84

1-Pyridin-3-yl-3-(2-quinolin-5-yl-2H-pyrazol-3-yl)-1H-pyridazin-4-one

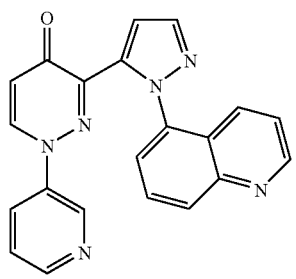 [SMILES: O=c1ccn(-c2cccnc2)nc1-c1ccnn1-c1cccc2ncccc12]

Pyridin-3-yl-3-(2-quinolin-5-yl-2H-pyrazol-3-yl)-1H-pyridazin-4-one was obtained in analogy to the method of example 1 from intermediate A-4 and quinolin-5-yl-hydrazine. MS: M=367.1 (M+H)⁺

Example 85

3-(2-Isoquinolin-5-yl-2H-pyrazol-3-yl)-1-(2-methyl-pyridin-4-yl)-1H-pyridazin-4-one

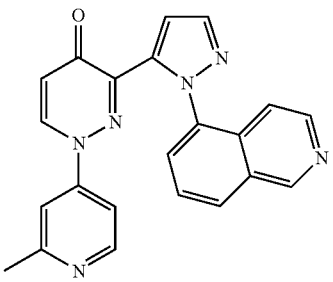 [SMILES: Cc1cc(-n2ccc(=O)c(-c3ccnn3-c3cccc4cnccc34)n2)ccn1]

3-(2-Isoquinolin-5-yl-2H-pyrazol-3-yl)-1-(2-methyl-pyridin-4-yl)-1H-pyridazin-4-one was obtained in analogy to the method of example 1 from intermediate A-6 and isoquinolin-5-yl-hydrazine. MS: M=381.3 (M+H)⁺

Example 86

3-(2-Isoquinolin-5-yl-2H-pyrazol-3-yl)-1-pyridin-3-yl-1H-pyridazin-4-one

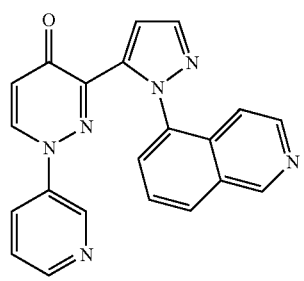 [SMILES: O=c1ccn(-c2cccnc2)nc1-c1ccnn1-c1cccc2cnccc12]

3-(2-Isoquinolin-5-yl-2H-pyrazol-3-yl)-1-pyridin-3-yl-1H-pyridazin-4-one was obtained in analogy to the method of example 1 from intermediate A-4 and isoquinolin-5-yl-hydrazine. MS: M=367.0 (M+H)⁺

Example 87

5-{3-[2-(2-Fluoro-phenyl)-2H-pyrazol-3-yl]-4-oxo-4H-pyridazin-1-yl}-nicotinonitrile

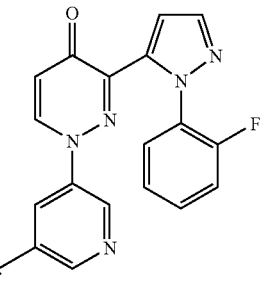

5-{3-[2-(2-Fluoro-phenyl)-2H-pyrazol-3-yl]-4-oxo-4H-pyridazin-1-yl}-nicotinonitrile was obtained in analogy to the method of example 1 from intermediate A-20 and 2-fluoro-phenylhydrazine. MS: M=359.1 (M+H)⁺

Example 88

1-(6-Chloro-pyridin-3-yl)-3-[2-(2-methyl-pyridin-4-yl)-2H-pyrazol-3-yl]-1H-pyridazin-4-one

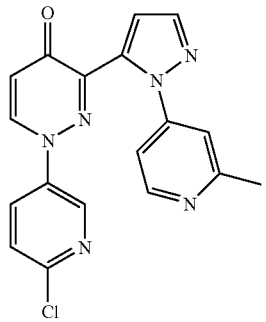 [SMILES: Cc1cc(-n2nccc2-c2nn(-c3ccc(Cl)nc3)ccc2=O)ccn1]

1-(6-Chloro-pyridin-3-yl)-3-[2-(2-methyl-pyridin-4-yl)-2H-pyrazol-3yl]-1H-pyridazin-4-one was obtained in analogy to the method of example 1 from intermediate A-18 and 2-methyl-pyridin-4-yl-hydrazine. MS: M=365.1 (M+H)⁺

Example 89

1-(5-Difluoromethoxy-pyridin-3-yl)-3-(2-quinolin-5-yl-2H-pyrazol-3-yl)-1H-pyridazin-4-one

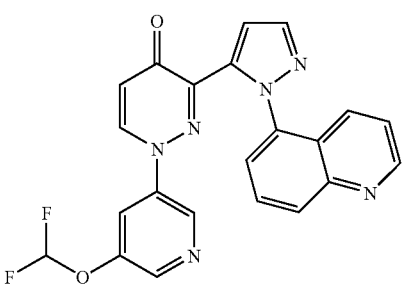 [SMILES: O=c1ccn(-c2cncc(OC(F)F)c2)nc1-c1ccnn1-c1cccc2ncccc12]

1-(5-Difluoromethoxy-pyridin-3-yl)-3-(2-quinolin-5-yl-2H-pyrazol-3-yl)-1H-pyridazin-4-one was obtained in analogy to the method of example 1 from intermediate A-15 and quinolin-5-yl-hydrazine. MS: M=433.2 (M+H)⁺

Example 90

3-[2-(2-Fluoro-phenyl)-2H-pyrazol-3-yl]-1-(5-methyl-pyridin-3-yl)-1H-pyridazin-4-one

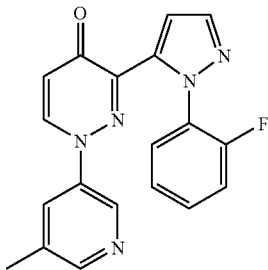 [SMILES: Cc1cncc(-n2ccc(=O)c(-c3ccnn3-c3ccccc3F)n2)c1]

3-[2-(2-Fluoro-phenyl)-2H-pyrazol-3-yl]-1-(5-methyl-pyridin-3-yl)-1H-pyridazin-4-one was obtained in analogy to the method of example 1 from intermediate A-5 and 2-fluoro-phenylhydrazine HCl. MS: M=348.2 (M+H)⁺

Example 91

3-[2-(7-Chloro-quinolin-4-yl)-2H-pyrazol-3-yl]-1-pyridin-4-yl-1H-pyridazin-4-one

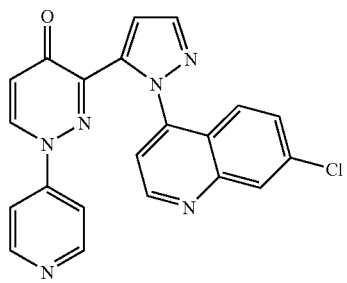 [SMILES: O=c1ccn(-c2ccncc2)nc1-c1ccnn1-c1ccnc2cc(Cl)ccc12]

3-[2-(7-Chloro-quinolin-4-yl)-2H-pyrazol-3-yl]-1-pyridin-4-yl-1H-pyridazin-4-one was obtained in analogy to the method of example 1 from intermediate A-1 and 7-chloro-quinolin-4-yl-hydrazine. MS: M=401.1 (M+H)⁻

Example 92

3-[2-(3-Methyl-pyridin-4-yl)-2H-pyrazol-3-yl]-1-pyridin-4-yl-1H-pyridazin-4-one

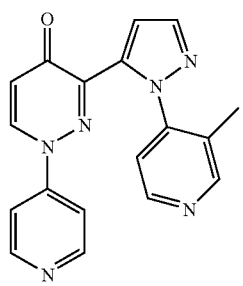 [SMILES: Cc1cnccc1-n1nccc1-c1nn(-c2ccncc2)ccc1=O]

3-[2-(3-Methyl-pyridin-4-yl)-2H-pyrazol-3-yl]-1-pyridin-4-yl-1H-pyridazin-4-one was obtained in analogy to the method of example 1 from intermediate A-1 and (3-methyl-pyridin-4-yl)-hydrazine. MS: M=331.1 (M+H)⁻

Example 93

3-[2-(2-Fluoro-phenyl)-2H-pyrazol-3-yl]-1-(2-methyl-pyridin-4-yl)-1H-pyridazin-4-one

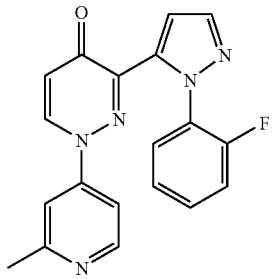 [SMILES: Cc1cc(-n2ccc(=O)c(-c3ccnn3-c3ccccc3F)n2)ccn1]

3-[2-(2-Fluoro-phenyl)-2H-pyrazol-3-yl]-1-(2-methyl-pyridin-4-yl)-1H-pyridazin-4-one was obtained in analogy to the method of example 1 from intermediate A-6 and 2-fluoro-phenylhydrazine HCl. MS: M=348.2 (M+H)⁺

Example 94

3-[2-(2-Fluoro-phenyl)-2H-pyrazol-3-yl]-1-(2-trifluoromethyl-pyridin-4-yl)-1H-pyridazin-4-one

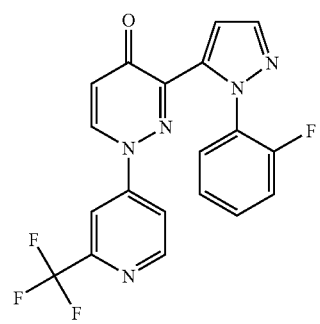 [SMILES: O=c1ccn(-c2ccnc(C(F)(F)F)c2)nc1-c1ccnn1-c1ccccc1F]

3-[2-(2-Fluoro-phenyl)-2H-pyrazol-3-yl]-1-(2-trifluoromethyl-pyridin-4-yl)-1H-pyridazin-4-one was obtained in analogy to the method of example 1 from intermediate A-21 and 2-fluoro-phenylhydrazine HCl. MS: M=402.1 (M+H)⁺

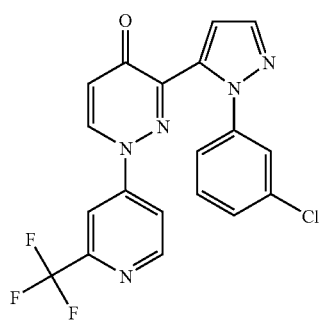 [SMILES: O=c1ccn(-c2ccnc(C(F)(F)F)c2)nc1-c1ccnn1-c1cccc(Cl)c1]

3-[2-(3-Chloro-phenyl)-2H-pyrazol-3-yl]-1-(2-trifluoromethyl-pyridin-4-yl)-1H-pyridazin-4-one was obtained in analogy to the method of example 1 from intermediate A-21 and 3-chloro-phenylhydrazine HCl. MS: M=418.1 (M+H)+

Example 96

4-{3-[2-(2-Fluoro-phenyl)-2H-pyrazol-3-yl]-4-oxo-4H-pyridazin-1-yl}-pyridine-2-carbonitrile

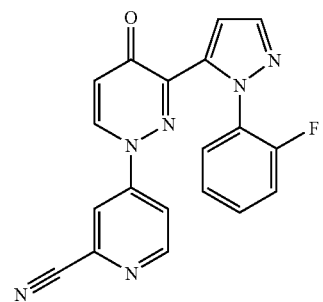 [SMILES: N#Cc1cc(-n2ccc(=O)c(-c3ccnn3-c3ccccc3F)n2)ccn1]

4-{3-[2-(2-Fluoro-phenyl)-2H-pyrazol-3-yl]-4-oxo-4H-pyridazin-1-yl}-pyridine-2-carbonitrile was obtained in analogy to the method of example 1 from intermediate A-9 and 2-fluoro-phenylhydrazine HCl. MS: M=359.1 (M+H)+

Example 97

3-[2-(3-Bromo-phenyl)-2H-pyrazol-3-yl]-1-pyridin-4-yl-1H-pyridazin-4-one

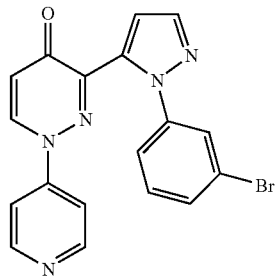 [SMILES: O=c1ccn(-c2ccncc2)nc1-c1ccnn1-c1cccc(Br)c1]

3-[2-(3-Bromo-phenyl)-2H-pyrazol-3-yl]-1-pyridin-4-yl-1H-pyridazin-4-one was obtained in analogy to the method of example 1 from intermediate A-1 and 3-bromo-phenylhydrazine HCl. MS: M=394.3 (M+H)+

Example 98

1-Pyridin-4-yl-3-[2-(3-trimethylsilanylethynyl-phenyl)-2H-pyrazol-3-yl]-1H-pyridazin-4-one

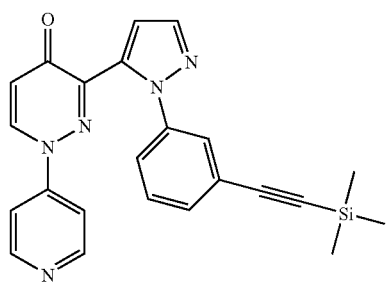 [SMILES: C[Si](C)(C)C#Cc1cccc(-n2nccc2-c2nn(-c3ccncc3)ccc2=O)c1]

A mixture of 3-[2-(3-Bromo-phenyl)-2H-pyrazol-3-yl]-1-pyridin-4-yl-1H-pyridazin-4-one (example 97, 81 mg, 0.21 mmol), ethynyltrimethylsilane (44 ul, 0.31 mmol), CuI (2 mg, 0.01 mmol), (PPh3)2PdCl2 (9 mg, 0.01 mmol), PPh3 (113 mg, 0.41 mmol) and dimethylamine (421 ul, 3.1 mmol of a solution in ethanol) in DMF (1.0 ml) is heated at 120° C. for 20 minutes under microwave irradiation. After purification of the crude product by preparative HPLC 33 mg (39% yield) of the product is obtained as solid material. MS: M=412.3 (M+H)+

Example 99

3-[2-(3-Ethynyl-phenyl)-2H-pyrazol-3-yl]-1-pyridin-4-yl-1H-pyridazin-4-one

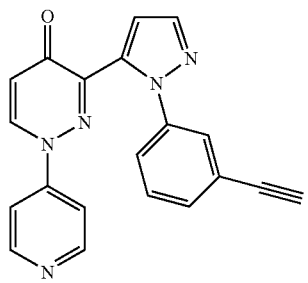 [SMILES: C#Cc1cccc(-n2nccc2-c2nn(-c3ccncc3)ccc2=O)c1]

A mixture of 1-Pyridin-4-yl-3-[2-(3-trimethylsilanylethynyl-phenyl)-2H-pyrazol-3-yl]-1H-pyridazin-4-one (example 98, 33 mg, 0.08 mmol) is dissolved in THF (1 ml). Tetrabutylammoniumfluoride trihydrate (51 mg, 0.16 mmol) is added at 0° C. and the reaction mixture is allowed to warm up to ambient temperature within 15 minutes. Stirring is continued for another 1 hour. The reaction mixture is quenched with water and extracted with ethyl acetate. The solvent is removed and the obtained crude product is purified by chromatography on silica gel using EtOAC/MeOH gradient to obtain 22 mg (81% yield) of the product. MS: M=340.1 (M+H)+

Example 100

3-[2-(2-Fluoro-phenyl)-2H-pyrazol-3-yl]-1-isoquinolin-6-yl-1H-pyridazin-4-one

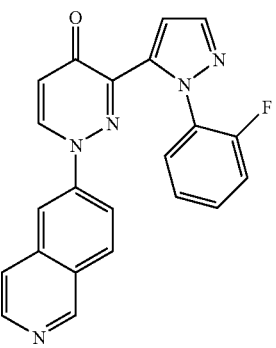 [SMILES: O=c1ccn(-c2ccc3cnccc3c2)nc1-c1ccnn1-c1ccccc1F]

3-[2-(2-Fluoro-phenyl)-2H-pyrazol-3-yl]-1-isoquinolin-6-yl-1H-pyridazin-4-one was obtained in analogy to the method of example 1 from intermediate A-22 and 2-fluorophenylhydrazine HCl. MS: M=384.2 (M+H)+

Example 101

3-[2-(3-Fluoro-phenyl)-2H-pyrazol-3-yl]-1-isoquinolin-6-yl-1H-pyridazin-4-one

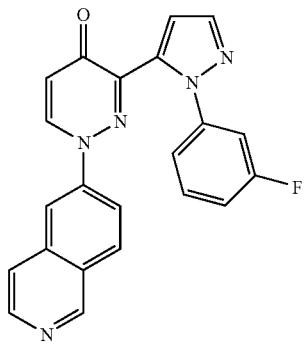 [SMILES: O=c1ccn(-c2ccc3cnccc3c2)nc1-c1ccnn1-c1cccc(F)c1]

3-[2-(3-Fluoro-phenyl)-2H-pyrazol-3-yl]-1-isoquinolin-6-yl-1H-pyridazin-4-one was obtained in analogy to the method of example 1 from intermediate A-22 and 3-fluorophenylhydrazine. MS: M=384.1 (M+H)$^+$

Example 102

3-[2-(2-Fluoro-phenyl)-2H-pyrazol-3-yl]-1-quinolin-6-yl-1H-pyridazin-4-one

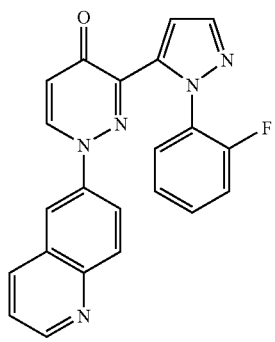 [SMILES: O=c1ccn(-c2ccc3ncccc3c2)nc1-c1ccnn1-c1ccccc1F]

3-[2-(2-Fluoro-phenyl)-2H-pyrazol-3-yl]-1-quinolin-6-yl-1H-pyridazin-4-one was obtained in analogy to the method of example 1 from intermediate A-23 and 2-fluorophenylhydrazine HCl. MS: M=384.1 (M+H)$^+$

Example 103

3-[2-(3-Chloro-phenyl)-2H-pyrazol-3-yl]-1-quinolin-6-yl-1H-pyridazin-4-one

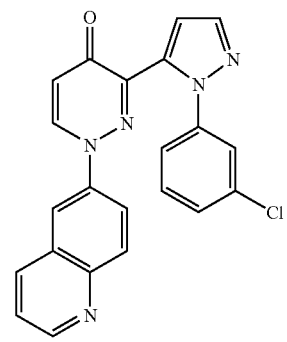 [SMILES: O=c1ccn(-c2ccc3ncccc3c2)nc1-c1ccnn1-c1cccc(Cl)c1]

3-[2-(3-Chloro-phenyl)-2H-pyrazol-3-yl]-1-quinolin-6-yl-1H-pyridazin-4-one was obtained in analogy to the method of example 1 from intermediate A-23 and 3-chlorophenylhydrazine HCl. MS: M=400.1 (M+H)$^+$

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Macrocrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxyde (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | ad 1.0 mL |

The active ingredient is dissolved in a mixture of Polyethylene Glycol 400 and water for injection (part). The pH is adjusted to 5.0 by Acetic Acid. The volume is adjusted to 1.0 mL by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:
1. A compound of formula (I)

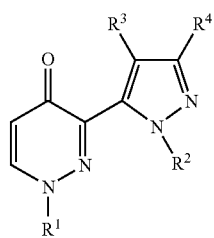

wherein
R$^1$ is pyridinyl, quinolinyl, or isoquinolinyl, each of which is optionally substituted with 1 to 4 substituents independently selected from the group consisting of lower-alkyl, lower-alkoxy, fluoro-lower-alkyl, fluoro-lower-alkoxy, lower-alkyl-SO$_2$, fluoro-lower-alkyl-SO$_2$, halogen, lower-alkoxy-lower-alkyl, cyano, NO$_2$, morpholinyl, NH$_2$—SO$_2$, NH(lower-alkyl)-SO$_2$, N(lower-alkyl)$_2$-SO$_2$, pyrrolidinyl-SO$_2$, piperidinyl-SO$_2$, morpholinyl-SO$_2$, hydroxy, COOH, COO-lower-alkyl, lower-alkyl-C(O)O, CO-lower-alkyl, CONH$_2$, CONH(lower-alkyl), CON(lower-alkyl)$_2$, lower-alkyl-CO—NH, lower-alkyl-CO—N(lower-alkyl), NH$_2$—CO-lower-alkyl, NH(lower-alkyl)-CO-lower-alkyl, N(lower-alkyl)$_2$-CO-lower-alkyl, NH$_2$, NH(lower-alkyl), N(lower-alkyl)$_2$, NH$_2$-lower-alkyl, NH(lower-alkyl)-lower-alkyl, N(lower-alkyl)$_2$-lower-alkyl, cycloalkyl, piperidinyl, piperazinyl and (N-lower-alkyl)-piperazinyl;
R$^2$ is aryl or heteroaryl, each of which is optionally substituted with 1 to 4 substituents independently selected from the group consisting of halogen, cyano, lower-alkyl, lower-alkoxy, fluoro-lower-alkyl, lower-alkynyl, lower-alkyl-SO$_2$, COOH, CONH$_2$, NH$_2$—SO$_2$, COO-lower-alkyl, lower-alkoxy-lower-alkyl, CONH(lower-alkyl), CON(lower-alkyl)$_2$, NH(lower-alkyl)-SO$_2$, N(lower-alkyl)$_2$-SO$_2$, lower-alkenyl, hydroxy, NO$_2$, morpholinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), NH$_2$—CO-lower-alkyl, NH(lower-alkyl)-CO-lower-alkyl, N(lower-alkyl)$_2$-CO-lower-alkyl, CO-lower-alkyl, NH$_2$, NH(lower-alkyl), N(lower-alkyl)$_2$, NH$_2$-lower-alkyl, NH(lower-alkyl)-lower-alkyl, N(lower-alkyl)$_2$-lower-alkyl, tri(lower-alkyl)silyl-loweralkynyl and cycloalkyl,
or wherein two substituents at adjacent positions on the aryl or heteroaryl are bound together to form a ring and said two bound substituents are lower-alkylene, dioxy-lower-alkylene, dioxy-fluoro-lower-alkylene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;

R$^3$ is hydrogen, lower-alkyl, fluoro-lower-alkyl, lower-alkoxy, fluoro-lower-alkoxy, halogen, hydroxy or phenyl; and
R$^4$ is hydrogen, lower-alkyl, fluoro-lower-alkyl, lower-alkoxy, fluoro-lower-alkoxy, halogen, hydroxy or phenyl;
or a pharmaceutically acceptable salt or ester thereof.
2. The compound of claim 1, wherein R$^1$ is pyridinyl, isoquinolinyl or quinolinyl, each of which is optionally substituted with 1 to 3 substituents independently selected from the group consisting of lower-alkyl, lower-alkoxy, fluoro-lower-alkyl, fluoro-lower-alkoxy, lower-alkyl-SO$_2$, halogen, cyano, morpholinyl and hydroxy.
3. The compound of claim 2, wherein R$^1$ is pyridinyl or quinolinyl, each of which is optionally substituted with 1 to 2 substituents independently selected from the group consisting of lower-alkyl, fluoro-lower-alkyl, fluoro-lower-alkoxy, lower-alkyl-SO$_2$, halogen, morpholinyl and hydroxy.
4. The compound of claim 3, wherein R$^1$ is pyridin-4-yl, 2-chloro-pyridin-4-yl, 2-methansulfonyl-pyridin-4-yl, pyridin-3-yl, 5-methyl-pyridin-3-yl, 2-morpholin-4-yl-pyridin-4-yl, 2-hydroxy-pyridin-4-yl, 5-chloro-pyridin-3-yl, 5-trifluoromethyl-pyridin-3-yl, 5-difluoromethoxy-pyridin-3-yl, 6-trifluoromethyl-pyridin-3-yl, quinolin-3-yl or 2-methyl-pyridin-4-yl.
5. The compound of claim 1, wherein R$^2$ is aryl selected from the group consisting of phenyl and naphthyl or heteroaryl selected from the group consisting of pyridinyl, quinolinyl and isoquinolinyl, which aryl or heteroaryl is optionally substituted with 1 to 3 substituents independently selected from the group consisting of halogen, cyano, lower-alkyl, fluoro-lower-alkyl, COOH, NH$_2$—SO$_2$, COO-lower-alkyl, N(lower-alkyl)$_2$-SO$_2$, piperazinyl, (N-(ower-alkyl)-piperazinyl, lower-alkynyl and tri(lower-alkyl)silyl-loweralkynyl,
or wherein two substituents at adjacent positions on the aryl or heteroaryl are bound together to form a ring and said two bound substituents are dioxy-lower-alkylene.
6. The compound of claim 5, wherein R$^2$ is aryl selected from the group consisting of phenyl and naphthyl or heteroaryl selected from the group consisting of quinolinyl and isoquinolinyl, which aryl or heteroaryl is optionally substituted with 1 to 2 substituents independently selected from the group consisting of halogen and lower-alkynyl,
or wherein two substituents at adjacent positions on the aryl or heteroaryl are bound together to form a ring and said two bound substituents are dioxy-lower-alkylene.
7. The compound of claim 6, wherein R$^2$ is napthalen-1-yl, quinolin-4-yl, phenyl, benzo[1,3]dioxol-5-yl, 3-fluoro-phenyl, 2,3-dihydro-benzo[1,4]dioxin-6-yl, 3-chloro-phenyl, 2-fluoro-phenyl, 3-bromo-phenyl, 3-ethynyl-phenyl or isoquinolin-5-yl.
8. The compound of claim 1, wherein R$^2$ is aryl or heteroaryl, each of which is optionally substituted with 1 to 4 substituents independently selected from the group consisting of halogen, cyano, lower-alkyl, lower-alkoxy, fluoro-lower-alkyl, lower-alkynyl, lower-alkyl-SO$_2$, COOH, CONH$_2$, NH$_2$—SO$_2$, COO-lower-alkyl, lower-alkoxy-lower-alkyl, CONH(lower-alkyl), CON(lower-alkyl)$_2$, NH(lower-alkyl)-SO$_7$, N(lower-alkyl)$_2$-SO$_2$, lower-alkenyl, hydroxy, NO₂, morpholinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), NH₂—CO-lower-alkyl, NH(lower-alkyl)-CO-lower-alkyl, N(lower-alkyl)₂-CO-lower-alkyl, CO-lower-alkyl, NH₂, NH(lower-alkyl), N(lower-alkyl)₂, NH₂-lower-alkyl, NH(lower-alkyl)-lower-alkyl, N(lower-alkyl)₂-lower-alkyl and cycloalkyl, or wherein two substituents at adjacent positions on the aryl or heteroaryl are bound together to form a ring and said two bound substituents are lower-alkylene, dioxy-lower-alkylene, dioxy-fluoro-lower-alkylene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene.

9. The compound of claim 1, wherein R³ is hydrogen.

10. The compound of claim 1, wherein R⁴ is hydrogen.

11. The compound of claim 1, selected from the group consisting of
3-[2-(6-Chloro-pyridin-2-yl)-2H-pyrazol-3-yl]-1-pyridin-4-yl-1H-pyridazin-4-one,
1-Pyridin-4-yl-3-(2-pyridin-2-yl-2H-pyrazol-3-yl)-1H-pyridazin-4-one,
3-[5-(4-Oxo-1-pyridin-4-yl-1,4-dihydro-pyridazin-3-yl)-pyrazol-1-yl]-benzonitrile,
3-[2-(2-Fluoro-phenyl)-2H-pyrazol-3-yl]-1-pyridin-4-yl-1H-pyridazin-4-one,
3-[5-(4-Oxo-1-pyridin-4-yl-1,4-dihydro-pyridazin-3-yl)-pyrazol-1-yl]-benzoic acid,
3-[2-(4-Chloro-phenyl)-2H-pyrazol-3-yl]-1-pyridin-4-yl-1H-pyridazin-4-one,
3-[2-(4-Fluoro-phenyl)-2H-pyrazol-3-yl]-1-pyridin-4-yl-1H-pyridazin-4-one,
4-[5-(4-Oxo-1-pyridin-4-yl-1,4-dihydro-pyridazin-3-yl)-pyrazol-1-yl]-benzenesulfonamide,
3-[2-(3,5-Dichloro-pyridin-4-yl)-2H-pyrazol-3-yl]-1-pyridin-4-yl-1H-pyridazin-4-one, and
3-[5-(4-Oxo-1-pyridin-4-yl-1,4-dihydro-pyridazin-3-yl)-pyrazol-1-yl]-benzoic acid methyl ester,
or a pharmaceutically acceptable salt or ester thereof.

12. The compound of claim 1, selected from the group consisting of
1-Pyridin-4-yl-3-(2-p-tolyl-2H-pyrazol-3-yl)-1H-pyridazin-4-one,
3-[2-(2-Chloro-phenyl)-2H-pyrazol-3-yl]-1-pyridin-4-yl-1H-pyridazin-4-one,
1-(2-Chloro-pyridin-4-yl)-3-(2-naphthalen-1-yl-2H-pyrazol-3-yl)-1H-pyridazin-4-one,
3-[2-(2,8-Bis-trifluoromethyl-quinolin-4-yl)-2H-pyrazol-3-yl]-1-pyridin-4-yl-1H-pyridazin-4-one,
3-[2-(2,3-Dihydro-benzo[1,4]dioxin-6-yl)-2H-pyrazol-3-yl]-1-pyridin-4-yl-1H-pyridazin-4-one,
1-(2-Methanesulfonyl-pyridin-4-yl)-3-(2-naphthalen-1-yl-2H-pyrazol-3-yl)-1H-pyridazin-4-one,
3-[2-(2,3-Dihydro-benzo[1,4]dioxin-6-yl)-2H-pyrazol-3-yl]-1-(2-methanesulfonyl-pyridin-4-yl)-1H-pyridazin-4-one,
3-[2-(3-Chloro-phenyl)-2H-pyrazol-3-yl]-1-pyridin-4-yl-1H-pyridazin-4-one,
3-[2-(2-Methyl-pyridin-4-yl)-2H-pyrazol-3-yl]-1-pyridin-4-yl-1H-pyridazin-4-one, and
1-Pyridin-4-yl-3-(2-quinolin-4-yl-2H-pyrazol-3-yl)-1H-pyridazin-4-one,
or a pharmaceutically acceptable salt or ester thereof.

13. The compound of claim 1, selected from the group consisting of
3-(2-Isoquinolin-5-yl-2H-pyrazol-3-yl)-1-pyridin-4-yl-1H-pyridazin-4-one,
1-Pyridin-4-yl-3-(2-quinolin-5-yl-2H-pyrazol-3-yl)-1H-pyridazin-4-one,
3-[2-(2-Chloro-pyridin-4-yl)-2H-pyrazol-3-yl]-1-pyridin-4-yl-1H-pyridazin-4-one,
3-{2-[2-(4-Methyl-piperazin-1-yl)-pyridin-4-yl]-2H-pyrazol-3-yl}-1-pyridin-4-yl-1H-pyridazin-4-one,
3-[2-(2-Piperazin-1-yl-pyridin-4-yl)-2H-pyrazol-3-yl]-1-pyridin-4-yl-1H-pyridazin-4-one,
1-Pyridin-4-yl-3-(2-quinolin-8-yl-2H-pyrazol-3-yl)-1H-pyridazin-4-one,
3-(2-Isoquinolin-8-yl-2H-pyrazol-3-yl)-1-pyridin-4-yl-1H-pyridazin-4-one,
N,N-Dimethyl-3-[5-(4-oxo-1-pyridin-4-yl-1,4-dihydro-pyridazin-3-yl)-pyrazol-1-yl]-benzenesulfonamide,
3-[2-(2,3-Difluoro-phenyl)-2H-pyrazol-3-yl]-1-pyridin-4-yl-1H-pyridazin-4-one, and
3-(2-Phenyl-2H-pyrazol-3-yl)-1-pyridin-4-yl-1H-pyridazin-4-one,
or a pharmaceutically acceptable salt or ester thereof.

14. The compound of claim 1, selected from the group consisting of
1-Pyridin-4-yl-3-(2-pyridin-4-yl-2H-pyrazol-3-yl)-1H-pyridazin-4-one,
3-(2-Benzo[1,3]dioxol-5-yl-2H-pyrazol-3-yl)-1-pyridin-3-yl-1H-pyridazin-4-one,
1-Pyridin-3-yl-3-(2-pyridin-2-yl-2H-pyrazol-3-yl)-1H-pyridazin-4-one,
3-[2-(2,3-Dihydro-benzo[1,4]dioxin-6-yl)-2H-pyrazol-3-yl]-1-pyridin-3-yl-1H-pyridazin-4-one,
3-[2-(3-Fluoro-phenyl)-2H-pyrazol-3-yl]-1-pyridin-3-yl-1H-pyridazin-4-one,
3-[2-(2,3-Dihydro-benzo[1,4]dioxin-6-yl)-2H-pyrazol-3-yl]-1-(5-methyl-pyridin-3-yl)-1H-pyridazin-4-one,
3-[2-(3-Fluoro-phenyl)-2H-pyrazol-3-yl]-1-(5-methyl-pyridin-3-yl)-1H-pyridazin-4-one,
3-[2-(2,3-Dihydro-benzo[1,4]dioxin-6-yl)-2H-pyrazol-3-yl]-1-(2-methyl-pyridin-4-yl)-1H-pyridazin-4-one,
3-[2-(3-Fluoro-phenyl)-2H-pyrazol-3-yl]-1-(2-methyl-pyridin-4-yl)-1H-pyridazin-4-one, and
3-[2-(3-Fluoro-phenyl)-2H-pyrazol-3-yl]-1-(2-methoxy-pyridin-4-yl)-1H-pyridazin-4-one,
or a pharmaceutically acceptable salt or ester thereof.

15. The compound of claim 1, selected from the group consisting of
3-[2-(2,3-Dihydro-benzo[1,4]dioxin-6-yl)-2H-pyrazol-3-yl]-1-(2-morpholin-4-yl-pyridin-4-yl)-1H-pyridazin-4-one,
3-[2-(3-Fluoro-phenyl)-2H-pyrazol-3-yl]-1-(2-morpholin-4-yl-pyridin-4-yl)-1H-pyridazin-4-one,
4-{3-[2-(2,3-Dihydro-benzo[1,4]dioxin-6-yl)-2H-pyrazol-3-yl]-4-oxo-4H-pyridazin-1-yl}-pyridine-2-carbonitrile,
4-{3-[2-(3-Fluoro-phenyl)-2H-pyrazol-3-yl]-4-oxo-4H-pyridazin-1-yl}-pyridine-2-carbonitrile,
3-[2-(3-Fluoro-phenyl)-2H-pyrazol-3-yl]-1-(5-methanesulfonyl-pyridin-3-yl)-1H-pyridazin-4-one,
3-[2-(2,3-Dihydro-benzo[1,4]dioxin-6-yl)-2H-pyrazol-3-yl]-1-(2-hydroxy-pyridin-4-yl)-1H-pyridazin-4-one,
3-[2-(2,5-Difluoro-phenyl)-2H-pyrazol-3-yl]-1-pyridin-3-yl-1H-pyridazin-4-one,
3-[2-(6-Fluoro-quinolin-4-yl)-2H-pyrazol-3-yl]-1-(5-methyl-pyridin-3-yl)-1H-pyridazin-4-one, 1-(5-Fluoro-pyridin-3-yl)-3-[2-(6-fluoro-quinolin-4-yl)-2H-pyrazol-3-yl]-1 pyridazin-4-one, and 3-[2-(6-Fluoro-quinolin-4-yl)-2H-pyrazol-3-yl]-1-pyridin-3-yl-1H-pyridazin-4-one, or a pharmaceutically acceptable salt or ester thereof.

16. The compound of claim 1, selected from the group consisting of 1-(5-Chloro-pyridin-3-yl)-3-(2-quinolin-4-yl-2H-pyrazol-3-yl)-1H-pyridazin-4-one, 1-(5-Chloro-pyridin-3-yl)-3-[2-(6-fluoro-quinolin-4-yl)-2H-pyrazol-3-yl]-1H-pyridazin-4-one, 3-[2-(3-Chloro-phenyl)-2H-pyrazol-3-yl]-1-(5-chloro-pyridin-3-yl)-1H-pyridazin-4-one, 1-(2-Chloro-pyridin-4-yl)-3-(2-quinolin-4-yl-2H-pyrazol-3-O-1H-pyridazin-4-one, 1-(2-Chloro-pyridin-4-yl)-3-[2-(6-fluoro-quinolin-4-yl)-2H-pyrazol-3-yl]-1H-pyridazin-4-one, 3-[2-(3-Chloro-phenyl)-2H-pyrazol-3-yl]-1-(2-chloro-pyridin-4-O-1H-pyridazin-4-one, 1-(2-Chloro-pyridin-4-yl)-3-[2-(2-chloro-pyridin-4-yl)-2H-pyrazol-3-yl]-1H-pyridazin-4-one, 1-(2-Chloro-pyridin-4-yl)-3-(2-quinolin-5-yl-2H-pyrazol-3-yl)-1H-pyridazin-4-one, 1-(2-Chloro-pyridin-4-yl)-3-(2-isoquinolin-5-yl-2H-pyrazol-3-yl)-1H-pyridazin-4-one, and 1-(5-Chloro-pyridin-3-yl)-3-(2-quinolin-5-yl-2H-pyrazol-3-yl)-1H-pyridazin-4-one, or a pharmaceutically acceptable salt or ester thereof.

17. The compound of claim 1, selected from the group consisting of 1-(5-Chloro-pyridin-3-yl)-3-[2-(6-chloro-quinolin-4-yl)-2H-pyrazol-3-yl]-1H-pyridazin-4-one, 1-(2-Chloro-pyridin-4-yl)-3-[2-(6-chloro-quinolin-4-yl)-2H-pyrazol-3-yl]-1H-pyridazin-4-one, 1-(2-Chloro-pyridin-4-yl)-3-[2-(2-fluoro-phenyl)-2H-pyrazol-3-yl]-1H-pyridazin-4-one, 1-(5-Chloro-pyridin-3-yl)-3-[2-(2-fluoro-phenyl)-2H-pyrazol-3-yl]-1H-pyridazin-4-one, 3-[2-(2-Fluoro-phenyl)-2H-pyrazol-3-yl]-1-isoquinolin-4-yl-1H-pyridazin-4-one, 3-[2-(3-Chloro-phenyl)-2H-pyrazol-3-yl]-1-isoquinolin-4-yl-1H-pyridazin-4-one, 3-[2-(3-Chloro-phenyl)-2H-pyrazol-3-yl]-1-(5-trifluoromethyl-pyridin-3-yl)-1H-pyridazin-4-one, 3-[2-(2-Fluoro-phenyl)-2H-pyrazol-3-yl]-1-(5-trifluoromethyl-pyridin-3-yl)-1H-pyridazin-4-one, 1-(2-Chloro-pyridin-4-yl)-3-[2-(7-chloro-quinolin-4-yl)-2H-pyrazol-3-yl]-1H-pyridazin-4-one, and 1-(5-Chloro-pyridin-3-yl)-3-[2-(7-chloro-quinolin-4-yl)-2H-pyrazol-3-yl]-1H-pyridazin-4-one, or a pharmaceutically acceptable salt or ester thereof.

18. The compound of claim 1, selected from the group consisting of 3-(2-Quinolin-4-yl-2H-pyrazol-3-yl)-1-(5-trifluoromethyl-pyridin-3-yl)-1H-pyridazin-4-one, 3-[2-(6-Chloro-quinolin-4-yl)-2H-pyrazol-3-yl]-1-pyridin-4-yl-1H-pyridazin-4-one, 3-(2-Isoquinolin-4-yl-2H-pyrazol-3-yl)-1-pyridin-4-yl-1H-pyridazin-4-one, 1-(5-Difluoromethoxy-pyridin-3-yl)-3-[2-(2-fluoro-phenyl)-2H-pyrazol-3-yl]-1H-pyridazin-4-one, 3-[2-(2-Fluoro-phenyl)-2H-pyrazol-3-yl]-1-(6-trifluoromethyl-pyridin-3-yl)-1H-pyridazin-4-one, 5-{3-[2-(2-Fluoro-phenyl)-2H-pyrazol-3-yl]-4-oxo-4H-pyridazin-1-yl}-pyridine-2-carbonitrile, 1-(6-Chloro-pyridin-3-yl)-3-[2-(2-fluoro-phenyl)-2H-pyrazol-3-yl]-1H-pyridazin-4-one, 3-[2-(2-Fluoro-phenyl)-2H-pyrazol-3-yl]-1-quinolin-3-yl-1H-pyridazin-4-one, 1-(2-Methyl-pyridin-4-yl)-3-(2-quinolin-4-yl-2H-pyrazol-3-yl)-1H-pyridazin-4-one, and 3-(2-Quinolin-5-yl-2H-pyrazol-3-yl)-1-(6-trifluoromethyl-pyridin-3-yl)-1H-pyridazin-4-one, or a pharmaceutically acceptable salt or ester thereof.

19. The compound of claim 1, selected from the group consisting of 3-(2-Isoquinolin-5-yl-2H-pyrazol-3-yl)-1-(6-trifluoromethyl-pyridin-3-yl)-1H-pyridazin-4-one, 3-[2-(7-Chloro-quinolin-4-yl)-2H-pyrazol-3-yl]-1-(5-methyl-pyridin-3-yl)-1H-pyridazin-4-one, 1-(2-Methyl-pyridin-4-yl)-3-(2-quinolin-5-yl-2H-pyrazol-3-yl)-1H-pyridazin-4-one, 1-Pyridin-3-yl-3-(2-quinolin-5-yl-2H-pyrazol-3-yl)-1H-pyridazin-4-one, 3-(2-Isoquinolin-5-yl-2H-pyrazol-3-yl)-1-(2-methyl-pyridin-4-yl)-1H-pyridazin-4-one, 3-(2-Isoquinolin-5-yl-2H-pyrazol-3-yl)-1-pyridin-3-yl-1H-pyridazin-4-one, 5-{3-[2-(2-Fluoro-phenyl)-2H-pyrazol-3-yl]-4-oxo-4H-pyridazin-1-yl}-nicotinonitrile, and 1-(6-Chloro-pyridin-3-yl)-3-[2-(2-methyl-pyridin-4-yl)-2H-pyrazol-3-yl]-1H-pyridazin-4-one, or a pharmaceutically acceptable salt or ester thereof.

20. The compound of claim 1, selected from the group consisting of 1-(2-Chloro-pyridin-4-yl)-3-(2-naphthalen-1-yl-2H-pyrazol-3-yl)-1H-pyridazin-4-one, 1-(2-Methanesulfonyl-pyridin-4-yl)-3-(2-naphthalen-1-yl-2H-pyrazol-3-yl)-1H-pyridazin-4-one, 1-Pyridin-4-yl-3-(2-quinolin-4-yl-2H-pyrazol-3-yl)-1H-pyridazin-4-one, 3-(2-Phenyl-2H-pyrazol-3-yl)-1-pyridin-4-yl-1H-pyridazin-4-one, 3-(2-Benzo[1,3]dioxol-5-yl-2H-pyrazol-3-yl)-1-pyridin-3-yl-1H-pyridazin-4-one, 3-[2-(3-Fluoro-phenyl)-2H-pyrazol-3-yl]-1-(5-methyl-pyridin-3-yl)-1H-pyridazin-4-one, 3-[2-(2,3-Dihydro-benzo[1,4]dioxin-6-yl)-2H-pyrazol-3-yl]-1-(2-morpholin-4-yl-pyridin-4-yl)-1H-pyridazin-4-one, 3-[2-(2,3-Dihydro-benzo[1,4]dioxin-6-yl)-2H-pyrazol-3-yl]-1-(2-hydroxy-pyridin-4-yl)-1H-pyridazin-4-one, 1-(5-Chloro-pyridin-3-yl)-3-(2-quinolin-4-yl-2H-pyrazol-3-yl)-1H-pyridazin-4-one, and 3-[2-(3-Chloro-phenyl)-2H-pyrazol-3-yl]-1-(2-chloro-pyridin-4-yl)-1H-pyridazin-4-one, or a pharmaceutically acceptable salt or ester thereof.

21. The compound of claim 1, selected from the group consisting of

3-[2-(3-Chloro-phenyl)-2H-pyrazol-3-yl]-1-(5-trifluoromethyl-pyridin-3-yl)-1H-pyridazin-4-one, 1-(5-Difluoromethoxy-pyridin-3-yl)-3-[2-(2-fluoro-phenyl)-2H-pyrazol-3-yl]-1H-pyridazin-4-one, 3-[2-(2-Fluoro-phenyl)-2H-pyrazol-3-yl]-1-(6-trifluoromethyl-pyridin-3-yl)-1H-pyridazin-4-one, 3-[2-(2-Fluoro-phenyl)-2H-pyrazol-3-yl]-1-quinolin-3-yl-1H-pyridazin-4-one, 1-(2-Methyl-pyridin-4-yl)-3-(2-quinolin-4-yl-2H-pyrazol-3-yl)-1H-pyridazin-4-one, and 3-(2-Isoquinolin-5-yl-2H-pyrazol-3-yl)-1-(2-methyl-pyridin-4-yl)-1H-pyridazin-4-one, or a pharmaceutically acceptable salt or ester thereof.

22. The compound of claim 1, selected from the group consisting of 1-(5-Difluoromethoxy-pyridin-3-yl)-3-(2-quinolin-5-yl-2H-pyrazol-3-yl)-1H-pyridazin-4-one, 3-[2-(2-Fluoro-phenyl)-2H-pyrazol-3-yl]-1-(5-methyl-pyridin-3-yl)-1H-pyridazin-4-one,
3-[2-(7-Chloro-quinolin-4-yl)-2H-pyrazol-3-yl]-1-pyridin-4-yl-1H-pyridazin-4-one,
3-[2-(3-Methyl-pyridin-4-yl)-2H-pyrazol-3yl]-1-pyridin-4-yl-1H-pyridazin-4-one,
3-[2-(2-Fluoro-phenyl)-2H-pyrazol-3-yl]-1-(2-methyl-pyridin-4-yl)-1H-pyridazin-4-one,
3-[2-(2-Fluoro-phenyl)-2H-pyrazol-3-yl]-1-(2-trifluoromethyl-pyridin-4-yl)-1H-pyridazin-4-one,
3-[2-(3-Chloro-phenyl)-2H-pyrazol-3-yl]-1-(2-trifluoromethyl-pyridin-4-yl)-1H-pyridazin-4-one,
4-{3-[2-(2-Fluoro-phenyl)-2H-pyrazol-3-yl]-4-oxo-4H-pyridazin-1-yl}-pyridine-2-carbonitrile,
3-[2-(3-Bromo-phenyl)-2H-pyrazol-3-yl]-1-pyridin-4-yl-1H-pyridazin-4-one,
1-Pyridin-4-yl-3-[2-(3-trimethylsilanylethynyl-phenyl)-2H-pyrazol-3-yl]-1H-pyridazin-4-one,
3-[2-(3-Ethynyl-phenyl)-2H-pyrazol-3-yl]-1-pyridin-4-yl-1H-pyridazin-4-one,
3-[2-(2-Fluoro-phenyl)-2H-pyrazol-3-yl]-1-isoquinolin-6-yl-1H-pyridazin-4-one,
3-[2-(3-Fluoro-phenyl)-2H-pyrazol-3-yl]-1-isoquinolin-6-yl-1H-pyridazin-4-one,
3-[2-(2-Fluoro-phenyl)-2H-pyrazol-3-yl]-1-quinolin-6-yl-1H-pyridazin-4-one, and
3-[2-(3-Chloro-phenyl)-2H-pyrazol-3-yl]-1-quinolin-6-yl-1H-pyridazin-4-one,
or a pharmaceutically acceptable salt or ester thereof.

23. The compound of claim 1, selected from the group consisting of
3-[2-(3-Bromo-phenyl)-2H-pyrazol-3-yl]-1-pyridin-4-yl-1H-pyridazin-4-one, and
3-[2-(3-Ethynyl-phenyl)-2H-pyrazol-3-yl]-1-pyridin-4-yl-1H-pyridazin-4-one,
or a pharmaceutically acceptable salt or ester thereof.

24. A pharmaceutical composition comprising a therapeutically effective amount of a compound of formula (I)

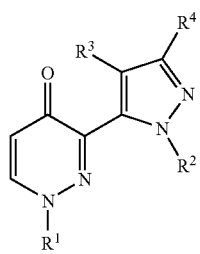

(I)

wherein
$R^1$ is pyridinyl, quinolinyl, or isoquinolinyl, each of which is optionally substituted with 1 to 4 substituents independently selected from the group consisting of lower-alkyl, lower-alkoxy, fluoro-lower-alkyl, fluoro-lower-alkoxy, lower-alkyl-SO$_2$, fluoro-lower-alkyl-SO$_2$, halogen, lower-alkoxy-lower-alkyl, cyano, NO$_2$, morpholinyl, NH$_2$—SO$_2$, NH(lower-alkyl)-SO$_2$, N(lower-alkyl)$_2$-SO$_2$, pyrrolidinyl-SO$_2$, piperidinyl-SO$_2$, morpholinyl-SO$_2$, hydroxy, COOH, COO-lower-alkyl, lower-alkyl-C(O)O, CO-lower-alkyl, CONH$_2$, CONH(lower-alkyl), CON(lower-alkyl)$_2$, lower-alkyl-CO—NH, lower-alkyl-CO—N(lower-alkyl), NH$_2$—CO-lower-alkyl, NH(lower-alkyl)-CO-lower-alkyl, N(lower-alkyl)$_2$-CO-lower-alkyl, NH$_2$, NH(lower-alkyl), N(lower-alkyl)$_2$, NH$_2$-lower-alkyl, NH(lower-alkyl)-lower-alkyl, N(lower-alkyl)$_2$-lower-alkyl, cycloalkyl, piperidinyl, piperazinyl and (N-lower-alkyl)-piperazinyl;
$R^2$ is aryl or heteroaryl, each of which is optionally substituted with 1 to 4 substituents independently selected from the group consisting of halogen, cyano, lower-alkyl, lower-alkoxy, fluoro-lower-alkyl, lower-alkynyl, lower-alkyl-SO$_2$, COOH, CONH$_2$, NH$_2$—SO$_2$, COO-lower-alkyl, lower-alkoxy-lower-alkyl, CONH(lower-alkyl), CON(lower-alkyl)$_2$, NH(lower-alkyl)-SO$_2$, N(lower-alkyl)$_2$-SO$_2$, lower-alkenyl, hydroxy, NO$_2$, morpholinyl, piperidinyl, piperazinyl, (N-lower-alkyl)-piperazinyl, pyrrolidinyl, lower-alkyl-C(O)O, lower-alkyl-CO—NH, lower-alkyl-CO—N(lower-alkyl), NH$_2$—CO-lower-alkyl, NH(lower-alkyl)-CO-lower-alkyl, N(lower-alkyl)$_2$-CO-lower-alkyl, CO-lower-alkyl, NH$_2$, NH(lower-alkyl), N(lower-alkyl)$_2$, NH$_2$-lower-alkyl, NH(lower-alkyl)-lower-alkyl, N(lower-alkyl)$_2$-lower-alkyl, tri(lower-alkyl)silyl-loweralkynyl and cycloalkyl,
or wherein two substituents at adjacent positions on the aryl or heteroaryl are bound together to form a ring and said two bound substituents are lower-alkylene, dioxy-lower-alkylene, dioxy-fluoro-lower-alkylene, NH-lower-alkylene, N(lower alkyl)-lower-alkylene, lower-alkylene-NH-lower-alkylene, lower-alkylene-N(lower alkyl)-lower-alkylene, NH—C(O)-lower-alkylene, N(lower alkyl)-C(O)-lower-alkylene, lower-alkylene-NH—C(O)-lower-alkylene, lower-alkylene-N(lower alkyl)-C(O)-lower-alkylene, C(O)—NH-lower-alkylene or C(O)—N(lower-alkyl)-lower-alkylene;
$R^3$ is hydrogen, lower-alkyl, fluoro-lower-alkyl, lower-alkoxy, fluoro-lower-alkoxy, halogen, hydroxy or phenyl; and
$R^4$ is hydrogen, lower-alkyl, fluoro-lower-alkyl, lower-alkoxy, fluoro-lower-alkoxy, halogen, hydroxy or phenyl;
or a pharmaceutically acceptable salt or ester thereof and a pharmaceutically acceptable carrier.

* * * * *

SEQUENCE LISTING

```
<160> NUMBER OF SEQ ID NOS: 2

<210> SEQ ID NO 1
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggggacaagt ttgtacaaaa aagcaggctt agtacctaga ggatcaagca tttgtacttc    60
agaag                                                                65

<210> SEQ ID NO 2
<211> LENGTH: 48
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 2
ggggaccact ttgtacaaga aagctgggtc aatcttcaga tgcagctg                 48
```